(12) United States Patent
Hobbs et al.

(10) Patent No.: US 11,284,823 B2
(45) Date of Patent: Mar. 29, 2022

(54) DEVICE AND METHOD FOR BLOOD VOLUME MEASUREMENT

(71) Applicant: Oregon Health & Science University, Portland, OR (US)

(72) Inventors: Theodore Hobbs, Portland, OR (US); Ravikant Samatham, Portland, OR (US); Steven L. Jacques, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 617 days.

(21) Appl. No.: 16/233,488

(22) Filed: Dec. 27, 2018

(65) Prior Publication Data

US 2019/0192060 A1 Jun. 27, 2019

Related U.S. Application Data

(60) Provisional application No. 62/610,609, filed on Dec. 27, 2017.

(51) Int. Cl.

| | |
|---|---|
| *A61B 5/1455* | (2006.01) |
| *A61B 5/145* | (2006.01) |
| *A61B 5/1459* | (2006.01) |
| *A61B 5/026* | (2006.01) |
| *A61B 5/0275* | (2006.01) |
| *A61B 5/00* | (2006.01) |
| *A61B 5/02* | (2006.01) |

(52) U.S. Cl.
CPC ........ *A61B 5/14556* (2013.01); *A61B 5/0071* (2013.01); *A61B 5/02028* (2013.01); *A61B 5/0261* (2013.01); *A61B 5/0275* (2013.01); *A61B 5/1459* (2013.01); *A61B 5/0075* (2013.01); *A61B 5/14535* (2013.01); *A61B 5/14552* (2013.01); *A61B 5/6831* (2013.01); *A61B 5/6832* (2013.01); *A61B 5/6852* (2013.01)

(58) Field of Classification Search
CPC .............. A61B 5/1455; A61B 5/14556; A61B 5/14552; A61B 5/14535; A61B 5/6831; A61B 5/6832

See application file for complete search history.

(56) References Cited

U.S. PATENT DOCUMENTS

| | | | |
|---|---|---|---|
| 5,024,231 A † | 6/1991 | Feldschuh | |
| 5,687,726 A * | 11/1997 | Hoeft | A61B 5/0275 600/323 |
| 5,697,371 A * | 12/1997 | Aoyagi | A61B 5/0275 600/479 |
| 6,280,386 B1 | 8/2001 | Alfano et al. | |

(Continued)

OTHER PUBLICATIONS

Levesque et al., (2009), "Plasma Disappearance Rate of Indocyanine Green: A Tool to Evaluate Early Graft Outcome After Liver Transplantation," Liver Transplantation, vol. 15, pp. 1358-1364. DOI: 10.1002/lt.21805.†

(Continued)

*Primary Examiner* — Eric F Winakur
(74) *Attorney, Agent, or Firm* — Schwabe, Williamson & Wyatt, P.C.

(57) ABSTRACT

Disclosed are a method, device and system for determining total circulating blood volume (BV) using a minimally invasive technique.

37 Claims, 11 Drawing Sheets

(56) References Cited

U.S. PATENT DOCUMENTS

| | | | |
|---|---|---|---|
| 6,339,714 B1* | 1/2002 | Chen | A61B 5/0086 600/314 |
| 2003/0032885 A1 | 2/2003 | Brunstein et al. | |
| 2005/0020891 A1* | 1/2005 | Rubinstein | A61B 5/029 600/315 |
| 2007/0078348 A1 | 4/2007 | Holman | |
| 2013/0079607 A1 | 3/2013 | Gareau et al. | |
| 2015/0327787 A1 | 11/2015 | Tognetti et al. | |
| 2018/0217168 A1† | 8/2018 | Feldschuh | |

OTHER PUBLICATIONS

Agenda of 2017 Military Health System Research Symposium, (2017), pp. 1-12.†

Pantanali et al., (2018), "Lessons Learned With the LiMON Method of Indocyanine Green Elimination," EC Gastroenterology and Digestive System, vol. 5.4, Mar. 30, 2018, pp. 297-304. DOI: 10.31080/ecgds.2018.05.00182.†

Wauters et al., (2007), "Non-Invasive Liver Monitoring in the Critically Ill: Plasma Disappearance Rate of Indocyanine Green (ICG-PDR)," Netherlands Journal of Critical Care, vol. 11, No. 2, Apr. 2007, pp. 92-98.†

Hobbs et al., (2017), "Rapid Blood Volume Measurement for Triage and Prolonged Field Care," 2017 Military Health System Research Symposium, Poster #071.†

Picker et al., (2001), "Determination of Total Blood Volume by Indicator Dilution: A Comparison of Mean Transit Time and Mass Conservation Principle," Intensive Care Medicine, vol. 27, No. 4, pp. 767-774. DOI: 10.1007/s001340100901.†

Listing of 2017 Military Health System Research Symposium Session 2 Posters, (2017), 8 pages.†

Sakka et al., (2000), "Comparison of Invasive and Noninvasive Measurements of Indocyanine Green Plasma Disappearance Rate in Critically Ill Patients With Mechanical Ventilation and Stable Hemodynamics," Intensive Care Medicine, vol. 26, No. 10, pp. 1553-1556. DOI: 10.1007/s001340000639.†

\* cited by examiner
† cited by third party

DEVICE AND METHOD FOR BLOOD VOLUME MEASUREMENT

CROSS-REFERENCE TO RELATED APPLICATION

This application claims the priority benefit of the earlier filing date of U.S. Provisional Patent Application No. 62/610,609, filed Dec. 27, 2017, which is specifically incorporated herein by reference in its entirety.

STATEMENT OF GOVERNMENT INTEREST

This invention was made with government support under UL1TR000128 and P51OD01192 awarded by the National Institutes of Health (NIH). The government has certain rights in the invention.

TECHNICAL FIELD

The present disclosure relates to the field of blood volume measurement. More specifically, to devices, systems, and methods for minimally invasive blood volume measurement.

BACKGROUND

Blood volume (BV) is a dynamic physiological parameter that may change rapidly and sometimes dramatically. These changes may be associated with blood loss, fluid retention, changes in vascular permeability, hormonal influences, or therapeutic interventions. While maintaining normal BV is essential in the management of chronic conditions such as congestive heart failure as well as critically ill patients, BV is rarely measured directly. Instead, physicians must rely upon surrogate indicators of BV such as hematocrit, blood pressure, and pulse rate. Physicians are frequently faced with the difficult decision to administer or withhold fluids, blood, and/or blood components on the basis of these surrogate tests. Unfortunately, these surrogate indicators can be misleading in the critical care setting because compensatory responses to acute BV derangements vary greatly among individuals and may occur at different rates. For example, a young and healthy individual may suffer significant acute blood loss yet their compensatory vasoconstriction may maintain blood pressure within the normal range. Hematocrit may also be normal immediately after acute blood loss. A robust compensatory response may maintain peripheral blood pressure at the expense of organ perfusion, which often results in renal failure or even multiple organ failure and death if resuscitative volume therapy is not instituted. Accurate and objective BV determination is critically important information that is currently missing from the diagnostic arsenal.

Traditional techniques that measure BV utilize indicator-dilution methodology. In 1980, the International Committee for Standardization in Hematology recommended the use of radioactive chromium within autologous red blood cell (RBC) to measure RBC volume and radioactive iodine bound to donor-derived human serum albumin to measure plasma volume as the "gold standard." However, this method was labor-intensive, error-prone, and clinically impractical. An alternative method was subsequently developed using radioiodinated human serum albumin to measure plasma volume and hematocrit to infer RBC volume and thus BV was determined by the sum of plasma and RBC volumes. This method compared favorably with the dual-isotope method and became the standard technique. Unfortunately, this method still required the injection of a radioactive isotope into patients followed by serial blood collection. These steps, along with laboratory processing using a large, expensive machine cluster that was typically housed in a nuclear medicine facility resulted in technical challenges and time delays that made this method of BV measurement impractical in clinical settings and impossible in field settings.

BRIEF DESCRIPTION OF THE DRAWINGS

Embodiments will be readily understood by the following detailed description in conjunction with the accompanying drawings and the appended claims. Embodiments are illustrated by way of example and not by way of limitation in the figures of the accompanying drawings.

DETAILED DESCRIPTION OF DISCLOSED EMBODIMENTS

Figure 1:
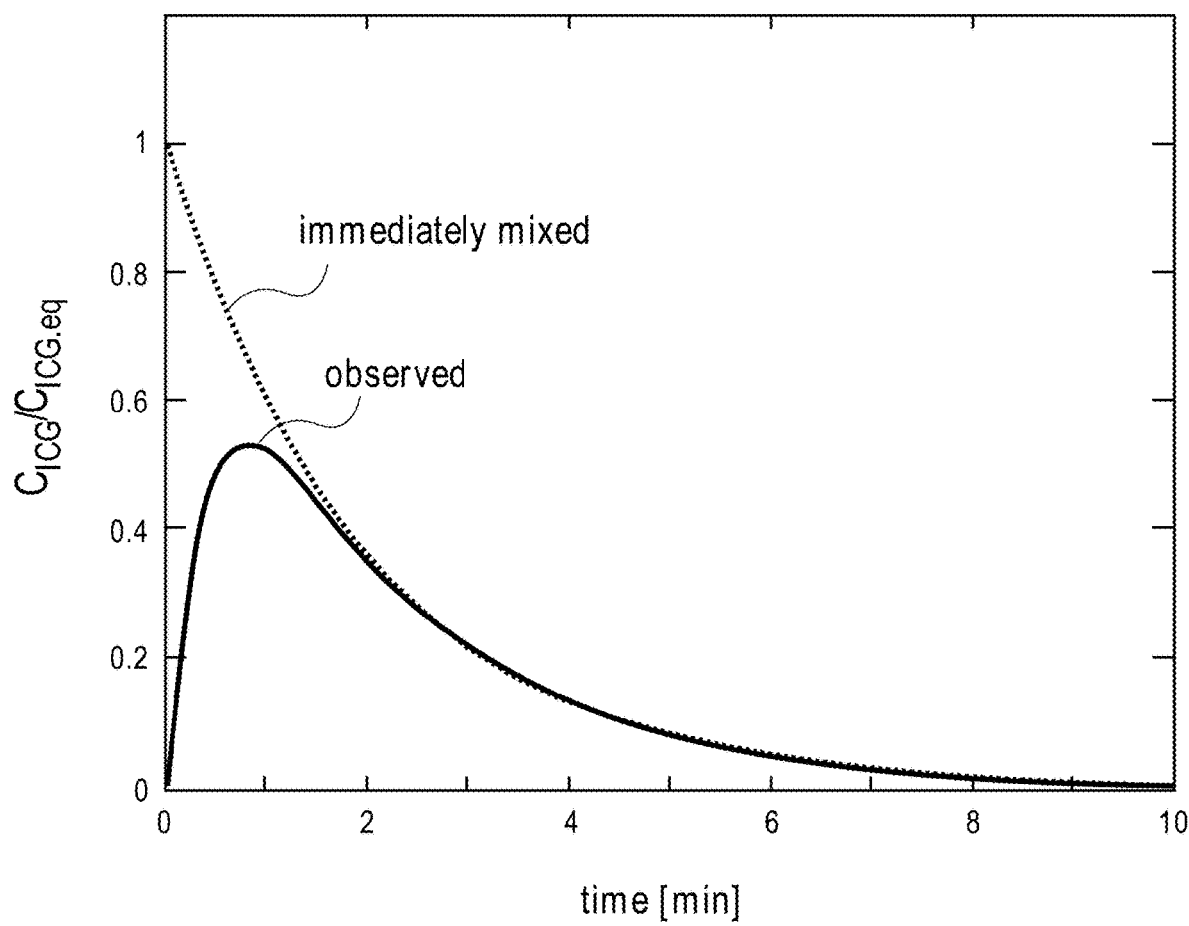
FIG. 1 shows the time course of relative Indocyanine green (ICG) concentrations in the blood, $C_{ICG}(t)/C_{ICG.eq}$. The dashed line shows the dilution of ICG if perfect mixing occurred immediately upon injection, starting at $C_{ICG.eq}$.

In the following detailed description, reference is made to the accompanying drawings, which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical contact with each other. "Coupled" may mean that two or more elements are in direct physical contact. However, "coupled" may also mean that two or more elements are not in direct contact with each other, but yet still cooperate or interact with each other. Coupled may also mean electronically coupled, such as wired or unwired.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.). The modifier "about" used in connection with a quantity is inclusive of the stated value and has the meaning dictated by the context (e.g., includes the degree of error associated with measurement of the particular quantity). In the context of this disclosure, the term "subject" refers to an animal, such as a mammal, that has been or will be the object of treatment, observation or experiment. The devices, systems and methods described herein may be useful in both human therapy and veterinary applications. In some embodiments, the subject is a mammal; in some embodiments, the subject is human.

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Introduction

Early identification of significant blood loss and the detection of ongoing blood loss are critical determinations in critical care settings. The maintenance of blood volume is essential in providing organ support in order to reduce morbidity and mortality during the acute treatment and prolonged damage control resuscitation phases of many injuries as well as conditions such as gastrointestinal hemorrhage and post-partum hemorrhage. While critically important, objective and immediate blood volume determination is currently impossible in many critical care environments. Civilian physicians and military medics must rely upon surrogate parameters such as blood pressure, hematocrit, and heart rate. These surrogate methods have been proven to be inaccurate or even misleading, resulting in preventable morbidity and mortality.

Objective blood volume determination is a promising diagnostic tool that could accurately direct resuscitation and triage decision-making as well as aid in judicious use of fluids and blood transfusions in austere environments. As disclosed herein the inventors have developed a novel device, system, and methods for the in vivo determination of blood volume. The device developed is small and durable enough to be used in the field or hospital settings to improve diagnostic accuracy and guide therapeutic decision-making.

The only commercially available device for blood volume measurement is the Blood Volume Analyzer, BVA-100 (Daxor Corporation, New York, N.Y.). The BVA-100 is a semiautomated system that uses radiolabeled human serum albumin ($^{131}$I-HSA) as a blood volume indicator. Daxor supplies this blood volume indicator in a dose syringe, marketed as Volumex®. A known quantity of $^{131}$I-HSA is injected into the circulation of the patient. After the blood volume indicator has mixed fully throughout the patient's circulatory system, a series of five consecutive blood samples are withdrawn at fixed time intervals. The known concentration of radioactivity equilibrates in circulation and the subsequent degree of dilution is directly proportional to the volume of the diluent. Concentration measurements from five consecutive blood draws allow a linear extrapolation of the concentrations to time zero, resulting in accurate volume determinations. A significant drawback of this method is that the radioactive isotope requires special licensing and handling. Exposure to personnel and patient are considerations. Exposure to radioactivity may also become an obstacle for patient consent. The diagnostic test and analysis are prolonged, taking 4-6 hours before results are available in some settings. In many cases, the clinical relevance of the results has long passed by the time these results are available. Additionally, the $^{131}$I-HSA remains in circulation for 18-28 hours, which precludes any repeat measurements during this period. Additional obstacles are the high purchase price of the Daxor machine cluster as well as the annual maintenance fees and the extensive laboratory space required to house these machines. Because the indicator is radioactive, the machines are typically housed within a nuclear medicine laboratory, which is not available in most hospitals. Furthermore, recent studies have indicated a bias towards overestimation of blood volume when HSA is used as a blood volume indicator for these measurements. The likely reason is a subset of HSA binds to albumin receptors on the endothelial cells lining the blood vessels, resulting in false dilution of the blood volume indicator. Given all of the problems with current methods of measuring blood volume, additional methods, systems, and devices are needed.

To meet the needs identified above, disclosed herein is a blood volume analyzer that uses an intravenously positioned optical fiber probe to measure the reflectance of an injected blood volume indicator. As disclosed herein, the device for determining BV is small, lightweight, and rugged, meeting the needs of a clinical or field ready device.

Blood volume is calculated by measuring the concentration of a blood volume indicator that is injected in the circulatory system (typically intravenously). The blood volume indicator concentration decreases with time as the blood volume indicator is metabolized or otherwise eliminated from circulation. The rate of elimination is used to calculate the blood volume by back extrapolating to a timepoint about 1 min after injection that specifies the concentration of ICG if all injected ICG were perfectly mixed. This extrapolated measured concentration of ICG equals the amount of injected ICG (volume injected x concentration injected) divided by the blood volume. Hence the blood volume is specified, as in equation 1 below. The present disclosure follows the dilution and elimination of a blood volume indicator in circulating blood, for example using optical-fiber technology that can be integrated with a standard intravenous catheter, as described below. The dilution of a blood volume indicator is directly proportional to diluent (blood) volume. Thus by being able to determine the degree to which a blood volume indicator is diluted allows for the determination of the total blood volume of a subject.

In certain embodiments, the device, system and methods uses indocyanine green (ICG), as the blood volume indicator. ICG mixes thoroughly and completely within the circulating compartment, then is eliminated within 15 minutes by the liver, then is excreted unchanged in the bile. Furthermore, ICG has been used for medical applications for many years, most recently for retinal angiography and liver function assessment. ICG does not cross the placenta and has been used in many pregnant women without any reports of harm to the fetus.

One of the advantageous aspects of the methods, systems and devices disclosed herein is that no blood sampling or laboratory processing is necessary as measurements are made in vivo. The in vivo detection methods disclosed herein provide blood volume reports within a few minutes, so the information would be available while it is clinically relevant. The rapid acquisition of patient blood volume will allow clinicians to utilize this information for immediate decision making as well as enable progressive monitoring of blood volume to assess the effectiveness of therapeutic interventions. By selecting a blood volume indicator that is rapidly eliminated from the body the test may be repeated every 15 minutes, enabling clinicians to monitor the effects of therapeutic interventions such as volume expansion in the treatment of vascular shock by comparing repeated measures over time.

The disclosed device is simple and easy to use. Objective BV can be determined by nurses in primary care facilities, emergency medical technicians in route to a hospital, or military medics in the field to make informed treatment decisions to help reduce acute secondary organ damage that often occurs after severe trauma and resuscitation. For trauma surgery applications, the quantification of intraoperative blood loss and the identification of ongoing blood loss, which are enabled by repeat measures capability (every 15 minutes), have direct impact on morbidity and mortality of trauma patients. In addition to trauma case management, it is anticipated fast and inexpensive BV determination will become standard practice in the management of shock, GI bleeds, major surgery, dialysis, chronic renal disease, syncope, and congestive heart failure. Another application is the calculation of chemotherapeutic drug dosing. Due to potential toxicities, the dosage of some chemotherapeutic drugs are based upon body surface area calculations, which are simply surrogates for BV. Measuring BV directly is far more accurate and safe than the use of a surrogate estimation.

Methods of Measuring Blood Volume

Disclosed herein is an in vivo dilution method for specifying the total blood volume fraction ($V_{tot}$) of an animal (including humans and other mammals), for example as implemented by a catheterized optical fiber probe (optical blood volume analyzer) disclosed herein. In embodiments, the optical probe is inserted in a blood vessel of a subject, such as a vein of the subject. While a vein is typically selected, an arterial vessel could be used or even a transdermal detector may be placed on the skin, similar to the finger clips used for pulse oximetry. A small volume, 1-10 mL of an indicator, such as indocyanine green (ICG), is injected into a blood vessel of the subject, typically not at the same vascular site as the optical probe. The device then follows the dilution and elimination of the indicator over time, for example by measuring the reflectance or fluorescence of the diluted indicator over time. This dilution and rate of elimination are analyzed, for example as described below, to yield the total blood volume ($BV_{tot}$ or $V_{tot}$). As used herein $BV_{tot}$ and $V_{tot}$ are synonyms.

When a small volume of an indicator (such as ICG) is intravascularly injected, the indicator will mix with the blood volume ($V_{tot}$) during circulation through the body and eventually equilibrate at a diluted concentration $C_{ICG.eq}$. Using ICG as an example, the equilibrium dilution of ICG is described as in Equation (1):

$$\frac{V_{inj}}{V_{tot}} = \frac{C_{ICG.eq}}{C_{ICG.inj}} \quad \text{(Equation 1)}$$

where $V_{tot}$=Total Blood Volume in the subject; $V_{inj}$=the total injected volume $C_{ICG.inj}$=the concentration of ICG injected and $C_{ICG.eq}$=the concentration of ICG at equilibrium.

However, after injection there will also be a gradual clearance of the blood volume indicator, such as ICG, from the blood for example by the liver. Therefore, the time-dependent concentration $C_{ICG}(t)$ can be described as in Equation (2):

$$C_{ICG}(t) = C_{ICG.0}\left(1 - e^{-\frac{t}{\tau_{mix}}}\right)e^{-\frac{t}{\tau_{clearance}}} \quad \text{(Equation 2)}$$

where $C_{ICG.0}$=the concentration of ICG at time 0 if the dye is mixed instantaneously; t is the time; and $\tau_{mix}$ and $\tau_{clearance}$ are time constants [min] that characterize the mixing that leads to final dilution and the clearance by the liver, respectively. Thus, $\tau_{clearance}$ is dependent on the specific indicator used. As discussed throughout this disclosure, the rate of clearance of the indicator may be useful for characterizing the liver function.

The early behavior of $C_{ICG}(t)$ will show fluctuations as the small volume of specific blood volume indicator first circulates and is not yet fully mixed (for example there may be portions of the blood that have greater concentrations of the blood volume indicator than others). At later times, however, the behavior will follow Equation (2). FIG. 1 shows the expected time course $C_{ICG}(t)$. In embodiments, determining total blood volume ($V_{tot}$) includes fitting the $C_{ICG}(t)$ data to Equation (2) to specify the 3 unknowns, $C_{ICG.0}$, $\tau_{mix}$ and $\tau_{clearance}$. The $C_{ICG.eq}$ is specified from the predicted $C_{ICG}(t)$ curve to calculate $V_{tot}$ using Equation 1.

The $C_{ICG.eq}$ is calculated by extrapolation of the later approximately linear portion of the $C_{ICG}(t)$ curve to a timepoint ($t_{eq}$) that typically occurs 1 min after the time of injection. At this timepoint $t_{eq}$, the extrapolated value specifies $C_{ICG.eq}$, which does not equal the peak of the $C_{ICG}(t)$ curve since at the peak the ICG is still not perfectly mixed and the optical probe sees a passing bolus of ICG. The time delay between $t_{eq}$ and the true time of injection ($t_{inj}$) is putatively due to a delay required for mixing before the onset of steady removal of ICG by the liver. The total blood volume is calculated using Equation (1).

The wavelength spectrum R(X) is simulated by computation, to illustrate a practical data acquisition and analysis. In certain embodiments the equations below are used to calculate $C_{ICG}(t)$ from reflectance data before injection of blood volume indicator into the blood (see FIG. 4, which shows ICG concentration as a function of time at a specific wavelength).

The parameters assumed in the computation are:
oxygen saturation of hemoglobin in vein $S=0.75$ (This is an initial estimation that is later optimized)
water content of blood $W=0.95$ (This is an initial estimation that is later optimized)
optical scattering coefficient of blood versus wavelength ($\lambda$ [nm]), where $\mu_s'$(500 nm)=10 cm$^{-1}$ $$\mu_s'(\lambda) = \mu_s'(500 \text{ nm})\left(\frac{\lambda}{500 \text{ nm}}\right)^{-1} \quad \text{(Equation 3)}$$

(This is scattering coefficient as a function of wavelength, normalized so that at 500 nm, $\mu_s'$=10 cm$^{-1}$. This scattering coefficient spectrum is known in advance based on published values in the literature. Just like the absorption coefficient is weighted by S and W (see Equation 4), (additional fit parameter to adjust the magnitude of $\mu_s'$ but the shape does not change.)
optical absorption coefficient [cm$^{-1}$]

$$\mu_a(\lambda) = S\mu_{a.oxy}(\lambda) + (1-S)\mu_{a.deoxy}(\lambda) + W\mu_{a.water}(\lambda) \quad \text{(Equation 4)}$$

reflectance collected by the optical probe [cm$^{-2}$] (See Farrell T J, M S Patterson. 1992. A diffusion theory model of spatially resolved, steady-state diffuse reflectance for the noninvasive determination of tissue optical properties in vivo. Med. Phys. 19(4):879-888) The $\mu_{a.oxy}(\lambda)$ is the absorption spectrum of fully oxygenated whole blood (150 g hemoglobin/liter), $\mu_{a.deoxy}(\lambda)$ is the absorption spectrum of fully deoxygenated whole blood, and $\mu_{a.water}(\lambda)$ is the absorption spectrum of water, which are known from the published literature. These three $\mu_a$ spectra are weighted by the hemoglobin oxygen saturation (S) and the water content (W) values in the vein, which are specified by analysis of the measured spectrum using least-squares fitting.

$$R_{beforeICG} = \text{get}R(\mu_a, \mu_s') \quad \text{(Equation 5)}$$

The following equations illustrate how to calculate the volume ($V_{inj}$) of stock ICG solution injected in to the vein. Generally, we have a stock solution of ICG with certain concentration ($C_{ICG.stock}$). In embodiments $V_{inj}$ is chosen such that the mass of ICG injected is below $m_{ICG.allowed}$. Based on the mass of the subject body weight and the concentration of the stock solution the $V_{inj}$ value is adjusted to maintain an ICG mass below $m_{ICG.allowed}$.
mass [g] of ICG injection allowed $m_{ICG.allowed}$=0.00025 g/Kg·body·weight mass of monkey body weight $K_{gbw}$=10 Kg mass of ICG that can be injected $m = m_{ICG.allowed} K_{gbw}$=0.0025 g molecular weight of ICG MW=775 g/mole Concentration of stock ICG solution:

$C_{ICG.stock}$=0.0032 M $V_{inj}$ can be calculated with this relationship $$V_{inj} = \frac{m[g]}{MW\left[\frac{g}{mole}\right]} \frac{1000\left[\frac{mL}{L}\right]}{C_{ICG.stock}\left[\frac{moles}{L}\right]} = 1 \text{ mL}$$

Figure 2:
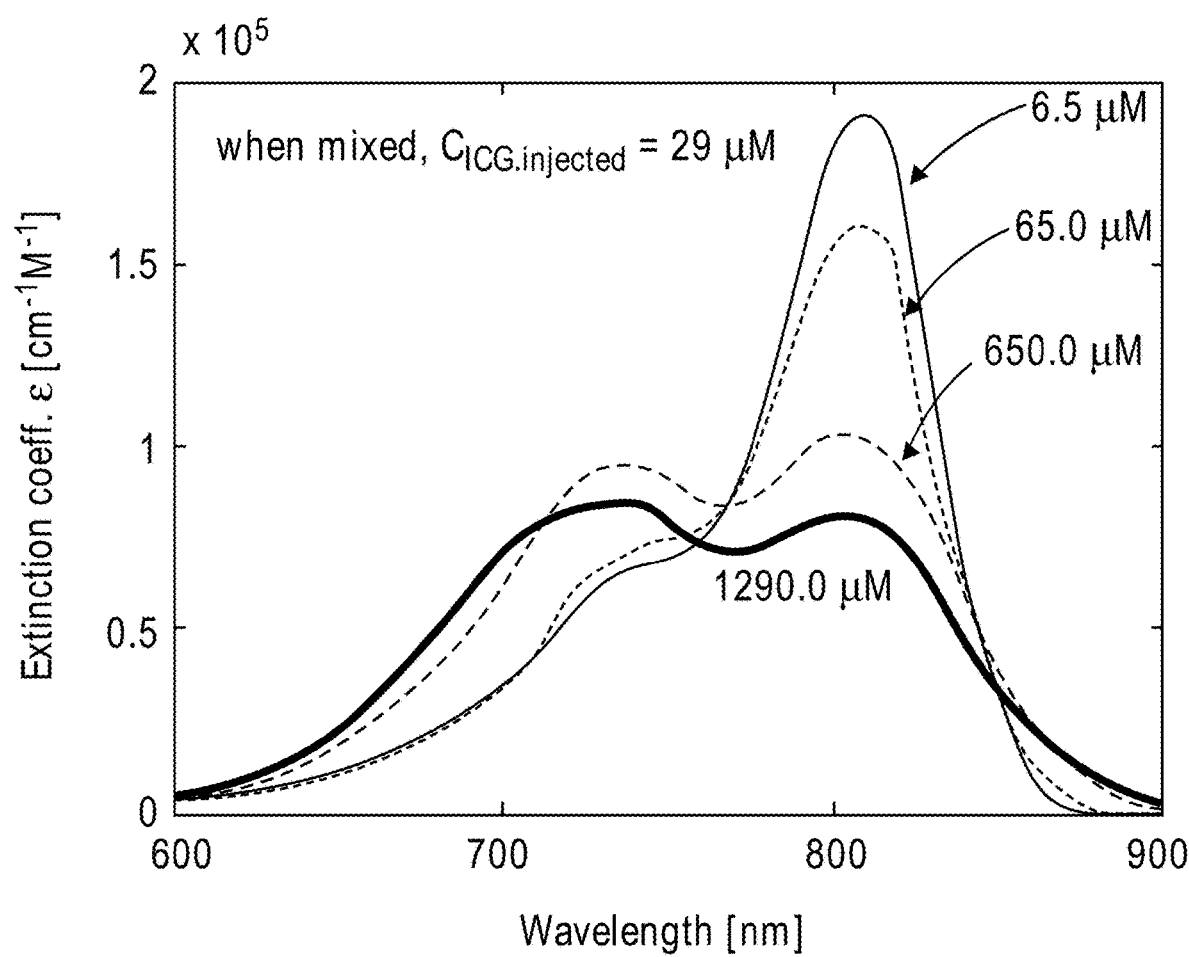
FIG. 2 shows the extinction coefficient (ε) of ICG in plasma, based on 1.2 mM concentration as taken from M. L. J. Landsman, G. Kwant, G. A. Mook, W. G. Zijlstra, "Light-absorbing properties, stability, and spectral stabilization of indocyanine green," *J. Appl. Physiol*, 40, 575-583 (1976).

The following equations are used to calculate $C_{icg}(t)$ from reflectance data after injection
extinction coefficient of ICG (see FIG. 2)

$\varepsilon_{ICG}(\lambda)$ absorption coefficient of ICG in blood $$\mu_{a.ICG}(t) = C_{ICG}(t)\varepsilon_{ICG}\ln(10) \text{ [cm}^{-1}] \quad \text{(Equation 6)}$$

reflectance collected by the optical probe $$R_{after.ICG}(t) = getR(\mu_a + \mu_{a.ICG}(t), \mu_s')$$ (Equation 7)

Figure 3:
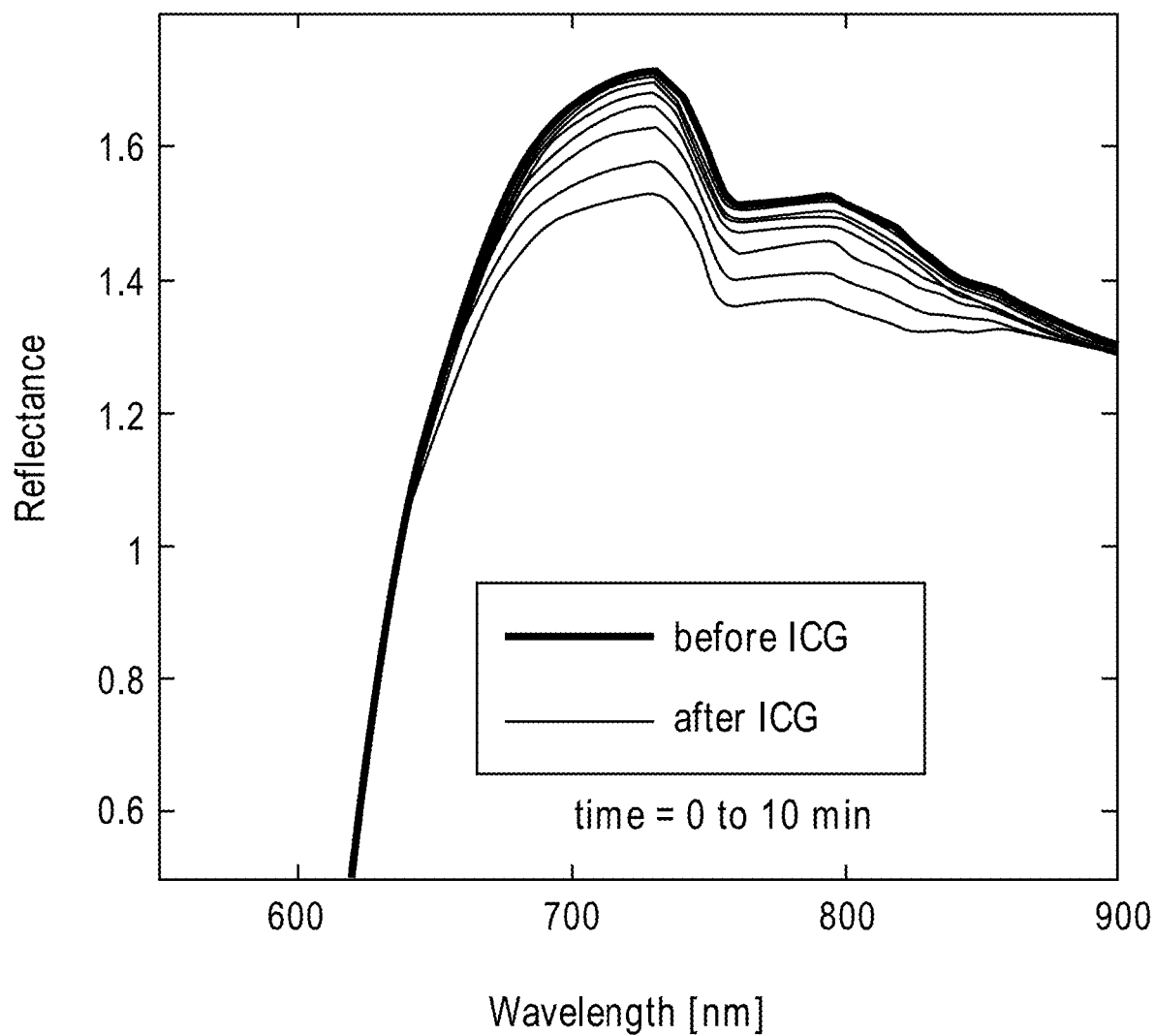
FIG. 3 shows the reflectance spectrum of blood, $R_{probe}(\lambda)$ [cm$^{-2}$], before and after injection of ICG.
Figure 4:
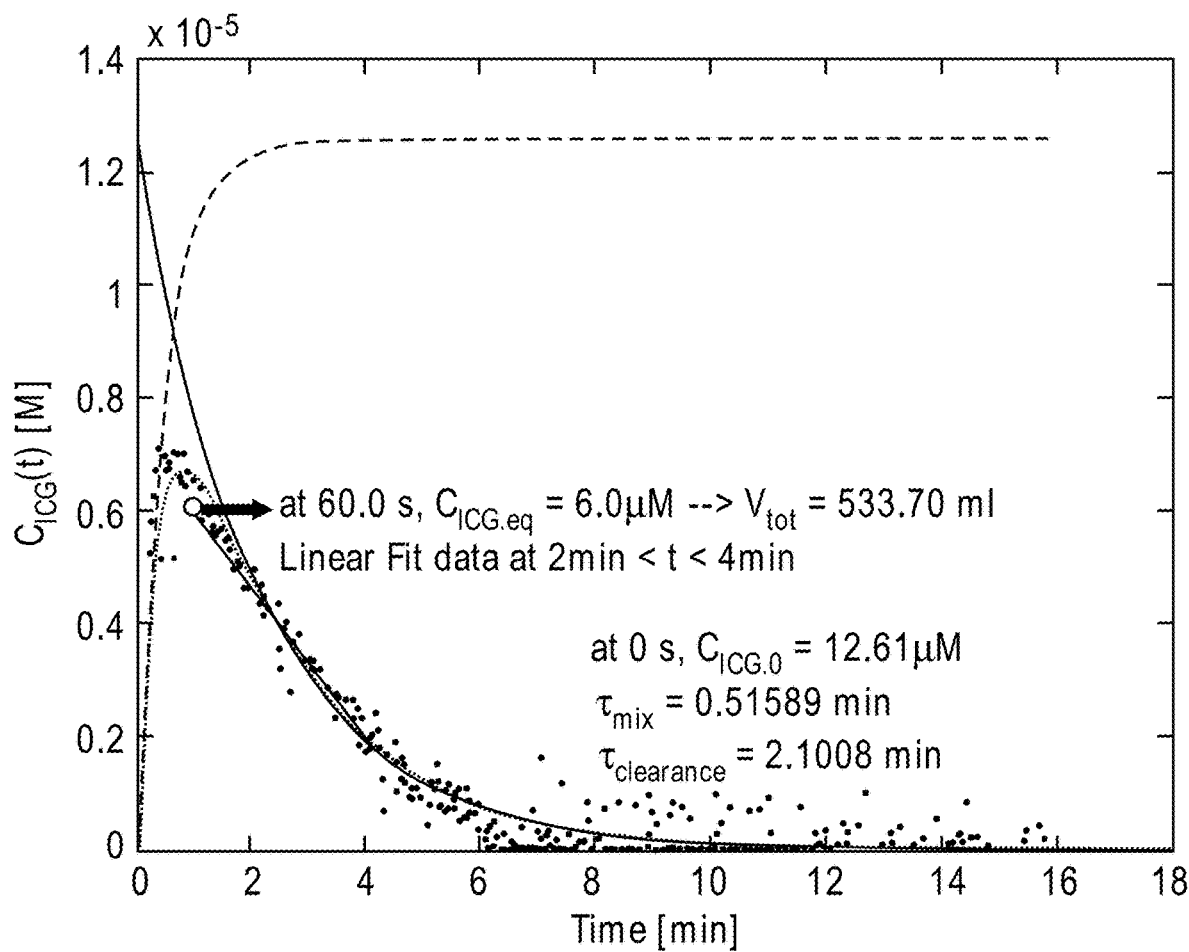
FIG. 4 shows the time course of ICG concentration specified from reflectance spectrum. The ICG concentration time course is fit by three parameters $C_{ICG.0}$, $\tau_{mix}$, and $\tau_{clearance}$. The ICG concentration at equilibrium ($C_{ICG.eq}$) is specified by extrapolating the linear portion of the ICG concentration time course to a timepoint ($t_{eq}$) which is typically 1 min after the injection time, when the dye is homogenously mixed in the blood, which is used to specify the total blood volume ($V_{tot}$).

The above model allows the reflectance spectrum $R(\lambda)$ to be calculated, as shown in FIG. 3 that depicts the spectra before and after injecting ICG. The above model is used to fit the measured reflectance spectrum to specify ICG concentration at each time point, generating a time course of an ICG concentration. FIG. 4 shows the time course of ICG concentration ($C_{ICG}(t)$). The $C_{ICG}(t)$ curve is fit with Equation (2) to specify $C_{ICG.0}$, $\tau_{mix}$ and $\tau_{clearance}$. Extrapolation of the approximately linear portion of the $C_{ICG}(t)$ curve to a timepoint ($t_{eq}$) that is typically 1 min after the injection time, specifies the equilibrium ICG concentration ($C_{ICG.eq}$) when the dye is homogenously mixed in blood, which applied to Equation (1) specifies the total blood volume ($V_{tot}$), the value of interest.

In summary, it is shown herein that an optical probe, for example having an optical fiber catheter inserted in a vein, can monitor the mixing and clearance of ICG injected into the vein. The analysis solves for two exponentials, and the value of total blood volume, $V_{tot}$. Thus disclosed herein is a method for optically determining the total blood volume, $V_{tot}$ in a subject, such as a human or veterinary subject (by veterinary subject it is meant any mammal, such as, but not limited to primates, dogs, cats, horses, and the like).

In embodiments, the method of measuring blood volume optically, includes administering, at a time 0, a blood volume indicator (BVI) at a known concentration and known volume into the blood of a subject, wherein the blood volume indicator has an optical readout; optically detecting a magnitude of the optical readout of the blood volume indicator as a function of time, wherein the magnitude of the optical readout decreases as a function of time as the blood volume indicator is eliminated from the blood of the subject; determining a time course for a concentration of blood volume indicator using the magnitude as a function of time; fitting the time course for the concentration of the blood volume indicator to the model:

$$C_{BVI}(t) = C_{BVI.0}\left(1 - e^{-\frac{t}{\tau_{mix}}}\right)e^{-\frac{t}{\tau_{clearance}}}$$

wherein $C_{BVI}(t)$ is the concentration of blood volume indicator at time t, $C_{BVI.0}$ is the concentration of ICG at time 0 if the dye mixed instantaneously, $\tau_{mix}$ is a mixing time constant of the blood volume indicator in blood and $\tau_{clearance}$ is a time constant for elimination of the blood volume indicator from the subject. The dye concentration at equilibrium $C_{BVI.eq}$ specified by extrapolating the approximately linear portion of the $C_{BVI}(t)$ curve to timepoint ($t_{eq}$) that is typically 1 min after the injection time, when the dye is homogenously mixed in blood, wherein the total blood volume ($V_{tot}$) is equal to the known concentration of the blood volume indicator multiplied by the known volume injected divided by the concentration of the blood volume indicator at equilibrium.

In embodiments, a reference reflectance spectrum is acquired prior to injection of the indicator, for example to calculate a pre-injection computed reflectance spectrum that matches the pre-injection reference reflectance spectrum acquired. In certain embodiments the method includes acquiring a pre-injection reflectance spectrum for use as a base line control. In certain embodiments the method includes, determining a pre-injection computed reflectance spectrum that simulates the pre-injection reflectance spectrum. In certain embodiments the method includes determining a pre-injection computed reflectance spectrum that simulates the pre-injection reflectance spectrum comprises modeling the pre-injection reflectance spectrum with $R_{before.BVI} = getR(\mu_a, \mu_s')$, wherein $$\mu_s'(\lambda) = \mu_s'(500 \text{ nm})\left(\frac{\lambda}{500 \text{ nm}}\right)^{-1}$$

as normalized at 500 nm and $\mu_a(\lambda) = S\,\mu_{a.oxy}(\lambda) + (1-S)\,\mu_{a.deoxy}(\lambda) + W\,\mu_{a.water}(\lambda)$. In embodiments, the optical absorption coefficient $\mu_a(\lambda)$ is determined according to Equation (4), with an initial guess for S and W. During this determination the absorption coefficient spectra $\mu_{a.oxy}(\lambda)$, $\mu_{a.deoxy}(\lambda)$, and $\mu_{a.water}(\lambda)$ are known (i.e., they are physical properties) and held constant. In embodiments, an optimization routine as notated in Equation (5) is used to iteratively calculate the pre-injection computed reflectance spectrum, adjusting the weighting values of S and W until the computed spectrum matches the experimentally measured pre-injection reflectance spectrum data. Note that the scattering coefficient spectrum $\mu_s'(\lambda)$ of Equation (3) is also used as input to the optimization routine—the scattering spectrum of Equation (3) is constant and normalized to a specific wavelength, for example a 500 nm wavelength. S, the oxygen saturation of hemoglobin in a vein is a clinically useful parameter that is recovered here. In other embodiments, the reference reflectance spectrum and/or the computed reflectance spectrum is a stored spectrum indicative spectrum of the subject.

Once the computed reflectance spectrum is determined, the blood volume indicator is injected into a blood vessel, such as a vein, of the subject. A set of post-injection reflectance datasets (individual post-injection reflectance spectrum at specific time points) are acquired over time. In certain embodiments, detecting a magnitude of the optical readout of the blood volume indicator is a function of time, includes acquiring a set of 2 or more post-injection reflectance spectra. In certain embodiments, the method includes determining a post injection computed reflectance spectrum for each of the 2 or more post-injection reflectance spectra. In certain embodiments, determining the post-injection computed reflectance spectrum that simulates the post-injection reflectance spectrum comprises modeling the post-injection reflectance spectrum with $R_{after.BVI}(t) = getR(\mu_a + \mu_{a.BVI}(t), \mu_s')$. where $\mu_{a.BVI}(t) = C_{BVI}(t)\,\varepsilon_{BVI}\ln(10)$ [cm$^{-1}$]. The number of data sets acquired is typically between at least 2 and 20, such as 2, 3, 4, 5, 6, 7, 8, 9, 10, 11, 12, 13, 14, 15, 16, 17, 18, 19, 20 or even more. The time interval over which the data sets can be acquired is typically long enough to calculate the elimination decay curve and thus extrapolate the blood volume at time of injection. The time period can be selected based on the blood volume agent or agents used, as some agents are eliminated faster than others.

For each of the individual post-injection reflectance spectrum dataset, optimizations are performed according to Equations (6) and (7). An initial guess is provided for S, W, $C_{ICG}$ and an optical absorption coefficient for ICG in blood $\mu_{a.ICG}(\lambda)$ is calculated according to Equation (6). An optimization routine as notated in Equation (7) is used to iteratively calculate individual post-injection computed reflectance spectra for each time point, adjusting the weighting values of S, W, and $C_{ICG}$ until the individual post-injection computed spectrum matches the individual measured post-injection reflectance spectrum at each time point. By determining the post-injection computed spectrum for each time point a set of set of S, W, and $C_{ICG}$ values is generated at each time point.

The set of $C_{ICG}$ values from each time point as described above is used to generate a time series $C_{ICG}(t)$ curve (i.e., concentration of ICG over time). The time series $C_{ICG}(t)$ curve is fit by Equation (2) to determine the values for CICG.0, $\tau_{mix}$ and $\tau_{clearance}$. The extrapolation of the linear portion of the $C_{ICG}(t)$ curve to timepoint ($t_{eq}$) of 1 min after the injection time specifies $C_{ICG.eq}$ used in Equation (1) to determine $V_{tot}$. The $V_{tot}$ is the total blood volume calculated by the disclosed method. In addition to the determining the total blood volume, the analysis also gives $\tau_{clearance}$ is also a clinically useful parameter characterizing liver function.

To optically measure the concentration of the blood volume indicator over the dilution time course, for example $C_{ICG}(t)$, a spectrum of collected light is measured by an optical probe, such as a fiber optic probe which is inserted into a blood vessel through a vascular catheter.

In certain embodiments, more than one blood volume indicator is injected for the determination of the specific components of blood volume: total volume, circulating volume, the difference between total volume and circulating volume, the marginal pool, and/or glycocalyx. In certain embodiments, blood volume measurement is repeated over time to measure the effects of therapeutic interventions and/or to detect ongoing blood loss and/or fluid retention.

Blood volume indicators for this disclosure are preferably inert and biocompatible in that they don't alter the physiology of the patient being assessed. Rapid elimination and clearance via metabolism or filtration is preferred to allow for repeat measures at clinically-relevant time intervals.

In certain embodiments, the blood volume indicator is a fluorophore or chromophore that may be bound to another molecule, such as a polysaccharide, or contained within microbubbles. In certain embodiments, a blood volume indicator is indocyanine green (ICG, Patheon Italia S.p.A., 20900 Mona (MB), Italy). While not being bound by theory, it is believed that ICG binds to blood proteins, mostly albumin, immediately upon intravenous injection, and thereby remains in the intravascular compartment until taken up by the liver and expelled in the bile. Another blood volume indicator is fluorescein isothiocyanate (FITC). In embodiments, FITC may be bound to a large polysaccharide such as hydroxyethyl starch (FITC-HES) or a dextran (FITC-Dextran) that stays within the intravascular compartment due to their large molecular sizes. These large polysaccharides are used for clinically (at much larger doses) to promote blood volume expansion. These may stay in circulation for 24-48 hours, so repeat measures would be complicated by artifacts from previous measures. Another viable blood volume indicator option that addresses the problem of prolonged retention in the circulatory compartment is the use of lipophilic microbubbles that contain FITC. Microbubbles and FITC-containing microbubbles are currently used for contrast ultrasound imaging. Microbubbles are removed from circulation by the liver within 15-20 minutes after injection. The blood volume indicators referenced herein may be used in any pharmaceutically acceptable formulation, medium, or carrier including, but not limited to, lyophilized, micellular, microbubble, lipid, and liposomal formulations The use of a combination of blood volume indicators may also yield clinically relevant information. For example, ICG and FITC-HES may be injected simultaneously: ICG binds to blood proteins and equilibrates with the vascular glycocalyx. FITC-HES is a much larger molecule and it does not equilibrate with the glycocalyx. For this reason, the volume determined by FITC-HES would be lesser than that determined by the ICG method. The difference between the two methods would be the total intravascular glycocalyx volume. Changes in the volume of the intravascular glycocalyx may be early indicators of atherosclerosis, stroke, chronic inflammation, or septic shock.

In some embodiments, in addition to the determination of BV additional clinically relevant parameters are determined and/or measured, for example hemoglobin (Hb) concentration, venous oxygen saturation ($SvO_2$), and/or lactate (or lactic acid). In embodiments, Hb concentration and $SvO_2$ are determined. In embodiments Hb concentration is used to calculate hematocrit (Hct), which is the proportion of the blood that is red cells. Hct is a percentage and Hb is reported in g/dl.

$$Hct = 3*(Hb)$$

BV and Hct are then used to calculate plasma volume (PV) and red cell volume (RV)

$$PV = BV(1-Hct)$$

$$RV = BV*Hct$$

Devices and Systems

Figure 5:
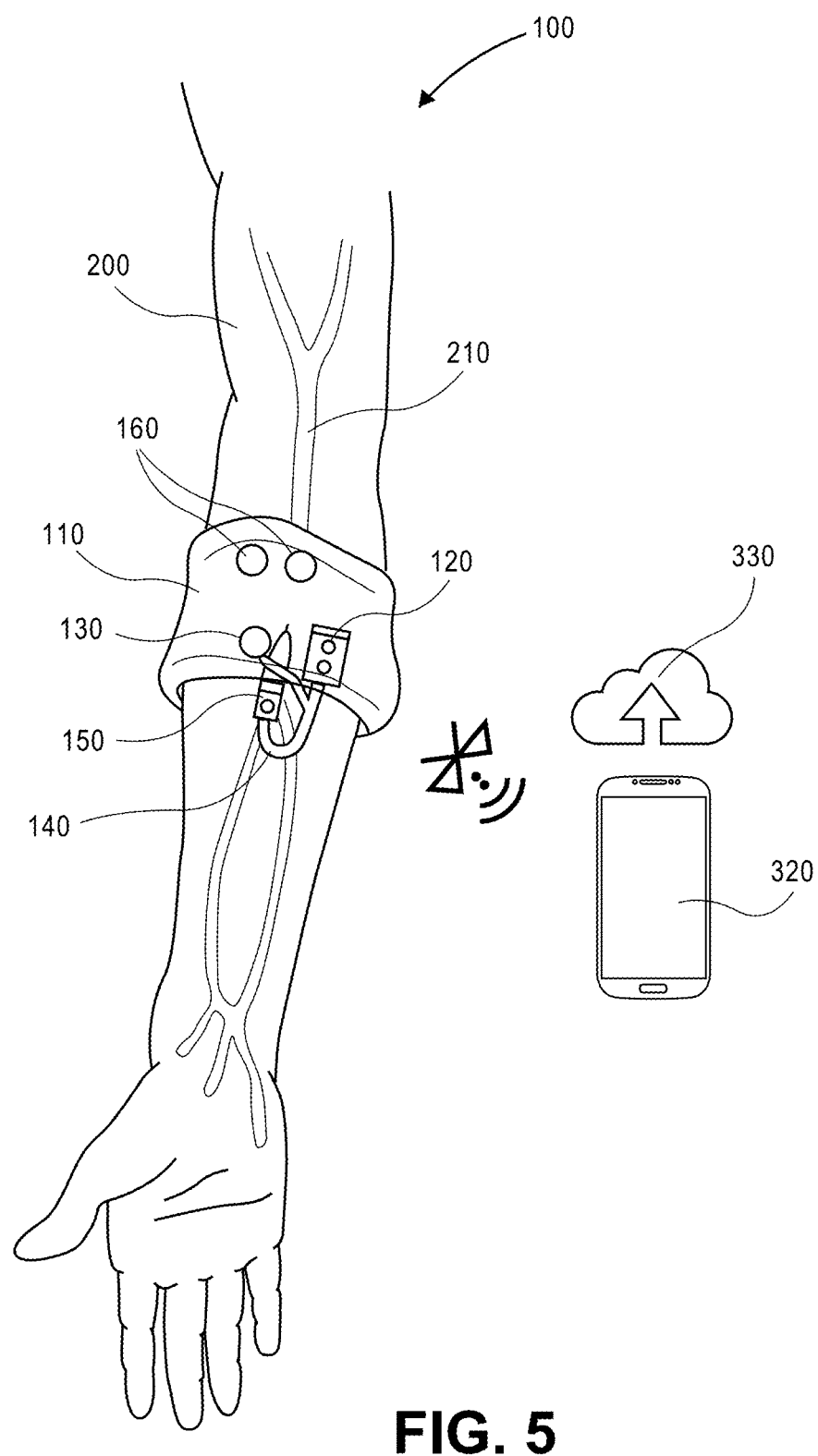
FIG. 5 shows a reusable armband with disposable optical fiber component that threads through a standard 22-ga intravenous catheter, in accordance with disclosed embodiments. As depicted, components embedded within the armband include an LED light source, mini-spectrometer and a controller. As depicted, the armband inhibits ambient light interference with the optical reflectance of the blood volume indicator. As depicted data are transmitted via to a mobile electronic device, such as a smart phone. In certain embodiment an app calculates blood volume results and may transmit the data and results to a Cloud for remote physician consultation.

FIG. 5, shows a mobile blood volume analyzer 100, in accordance with embodiments disclosed herein. The mobile blood volume analyzer 100 includes an armband 110 that attaches to the arm 200 of a subject, such as a durable armband. In some embodiments the armband 110 comprises materials and means that allow it to be attached to the arms of the subject and removed multiple times for repeated uses. In some embodiments, the armband 110 may be capable of passing around a subject's arm and secured in position through hook and loop means, such as a VELCRO® Brand hook and loop product. In other embodiments, the armband 110 may be secured on a subject's arm through an adjustable strap and buckle means. In some embodiments the armband 110 may be secured by a quick-release strap and buckle means. In even other embodiments, the device can be attached to the body of a subject, for example by a disposable adhesive patch that blocks ambient light and has a docking site for the device (see, for example, FIG. 12). Such adhesives and methods of their use are known in the art. In the embodiment shown, the armband 110 includes the components of the worn part of the mobile blood volume analyzer 100, including a mini-spectrophotometer 120 and a light source 130, such as a LED light source. The mobile blood volume analyzer 100 further includes a fiber optic cable 140 that couples the mini spectrophotometer 120 to an intravenous probe 150. The intravenous probe 150 is configured to capture the reflected light from an indicator that has been injected into the subject. In embodiments, intravenous probe 150 is configured to be disposable, for example configured for a single use, such as for a single subject. In certain embodiments, the fiber optic cable 140 is configured to be disposable and is reversibly coupled to the mini spectrophotometer 120, which is typically not configured to be a disposable component of the device. In other embodiments, the entire mobile blood volume analyzer 100 is configured to be disposable. In some embodiments, the mobile blood volume analyzer may be configured to display results on a small read-out screen, for example roughly the size of a watch face, in order to simplify and avoid the need for transmission to a smartphone or other device. The small read-out screen may attach via a docking site to a light-impermeable adhesive patch that is placed onto the skin, directly over the optical fiber terminus within the blood vessel (see, for example, FIG. 12). The mobile blood volume analyzer 100 may also include a monitoring component 160 coupled to the light source 130 and mini spectrophotometer 120. Light sources useful for this disclosure are associated with the peak absorption or excitation of the blood volume indicator(s) used, typically in the near infrared spectrum, 750 nm to 900 nm. Illumination sources may consist of one or more light emitting diodes (LEDs), lasers, or diode lasers. Illumination is transmitted to the detection site (intravascular) via optical fiber. In certain embodiments, the light detector is configured to detect, such that it is capable of detecting, reflectance or fluorescence of a blood volume indicator injected into the vascular compartment. In embodiments, the optical fiber is configured as two or more optical fibers. In certain embodiments the device includes two optical fibers, for example two optical fibers placed into a vessel lumen via intravascular catheter such that one fiber delivers light and the second fiber collects light. In certain embodiments a single optical fiber can be used. For example, for a single optical fiber, the optical fiber is placed into a vessel lumen via intravascular catheter such that the single fiber both delivers and collects light. In certain embodiments, the end of the optical fiber is beveled at an angle such that reflectance from the fiber/blood interface at an angle outside the numerical aperture of the fiber, and hence is not returned to the detector system. The detector system both launches light into the optical fiber and collects light from the optical fiber, which may be accomplished in a number of ways. In some embodiments, a beam splitter, also known as a fiber optic splitter, can couple the light source and detector to the optical fiber device. The fiber terminus for delivery and collection can be polished at an angle so that specular reflectance from the air/fiber interface during light injection into the fiber is not coupled back to the detector. In some embodiments, two smaller fibers, one from the light source and one connected to the detector, can be coupled to the larger fiber of the device. In some embodiments, a cluster of fibers method may be used. It is similar to the two-fiber method, but 1-3 central light emitter fibers are surrounded by several light detector fibers to increase the field of light detection. This may be configured in the opposite manner, with 1-3 central light detecting fibers surrounded by several light emitting fibers.

In embodiments, the optical blood volume analyzer includes an injector for injecting the blood volume indicator. The injector can be a syringe type injector that may be controlled by the components described herein, for example for automatic injection at time zero. In embodiments, the optical blood volume analyzer includes in injector extension, for example such that the indicator may be injected through the same IV catheter, for example, via a narrow cannula that is inserted parallel to, and extends "downstream" from, the optical fiber probe. In certain embodiments, the extension is retractable and/or removable, for example, to prohibit optical interference. In certain embodiments, the injector is a separate syringe type injector.

As depicted in FIG. 5, the mobile blood volume analyzer 100 distributes information to one or more networked devices 320 through one or more of network 330. Each network 330 includes a wired or wireless telecommunication means by which network systems (including systems mobile blood volume analyzer 100 and networked device 320) may communicate and exchange data. For example, each network 330 may be implemented as, or may be a part of, a storage area network (SAN), personal area network (PAN), a metropolitan area network (MAN), a local area network (LAN), a wide area network (WAN), a wireless local area network (WLAN), a virtual private network (VPN), an intranet, an Internet, a mobile telephone network, such as Global System for Mobile Communications (GSM), General Packet Radio Service (GPRS), cdmaOne, CDMA2000, Evolution-Data Optimized (EV-DO), Enhanced Data Rates for GSM Evolution (EDGE), Universal Mobile Telecommunications System (UMTS), Digital Enhanced Cordless Telecommunications (DECT), Digital AMPS (IS-136/TDMA), and Integrated Digital Enhanced Network (iDEN), Long-Term Evolution (LTE), $3^{rd}$ generation mobile network (3G), 4th generation mobile network (4G), and/or 5th generation mobile network (5G) networks, a card network, Bluetooth, near field communication network (NFC), any form of standardized radio frequency, or any combination thereof, or any other appropriate architecture or system that facilitates the communication of signals, data, and/or messages (generally referred to as data). Throughout this specification, it should be understood that the terms "data" and "information" are used interchangeably herein to refer any form of information that can exist in a computer-based environment.

In an example embodiment, each network system (including the mobile blood volume analyzer 100 and the networked device 320) includes a monitoring component 160 having a communication component capable of transmitting and/or receiving data over the network 330. Networked device 320 may comprise a server, personal computer, mobile device (for example, notebook computer, tablet computer, netbook computer, personal digital assistant (PDA), video game device, GPS locator device, cellular telephone, Smartphone, or other mobile device), a television with one or more processors embedded therein and/or coupled thereto, or other appropriate technology that includes or is coupled to a web browser or other application for communicating via the network 330.

In embodiments the monitoring component 160 includes at least one processor that is capable of monitoring or detecting reflectance data obtained by the mini-spectrophotometer 120 and operating the light source 120. The processor may also be capable of monitoring or detecting reflectance data in real time. The processor may also capable of directing the transmission of this information to another device, such as one or more of the networked device 320, through the network 330. In certain examples, monitoring component 160 is also capable of receiving information from one or more of the networked device 320, through the network 330.

In an example embodiment, the monitoring component 160 has one or more processors embedded therein and/or coupled thereto, or other appropriate technology that can communicate via an electronic, magnetic, or radio frequency field between the monitoring component 160 and another device. In an example embodiment, the monitoring component 160 has processing capabilities, such as storage capacity/memory and one or more applications (not illustrated) that can perform a particular function such as any of the methods disclosed herein. In example embodiments the monitoring component 160 includes a network controller, such as a Bluetooth controller. The network controller may be capable of sending and receiving data, performing authentication and ciphering functions, and directing how the monitoring component 160 will listen for and send transmissions from the networked device 320 or configure monitoring component 160 into various power-save modes, for example according to the Bluetooth-specified procedures. In another example embodiment, the network controller is a Wi-Fi controller capable of performing similar functions.

In various embodiments, the monitoring component 160 may communicate with the networked device 320 via an antenna, for example communicatively coupled thereto. In an example embodiment, once the monitoring component is activated, the controller is notified of the state of readiness of monitoring component for transmission. In various embodiments, monitoring component 160 may output a radio signal through the antenna. On establishing a communication channel between monitoring component 160 and the networked device 320, information may be transferred to the networked device.

An example monitoring component 160 may comprise a memory element, which can exist within a removable smart chip or a secure digital ("SD") card or which can be embedded within a fixed chip on monitoring component 160. In certain example embodiments, Subscriber Identity Component ("SIM") cards may be used. In various embodiments, the memory element may allow a software application resident on the monitoring component 160.

In an example monitoring component 160 includes a processor. A processor can exist within a removable smart chip or can be embedded within a fixed chip on monitoring component 160. The application host processor may comprise applications running thereon that perform the functionality described herein.

In certain embodiments, the networked device 320 is selected from the group of a cell phone, a smart phone, a personal computer, and a personal digital assistant. In certain embodiments, the networked device 320 is a mobile computing device (for example, a smartphone, such as an iPhone). In certain embodiments, the mobile computing device comprises a smart phone, such as a commercially available smart phone, for example an iPhone®, Samsung Galaxy®, Nokia Lumina® Motorola Droid® and the like. In some embodiments, the networked device 320 also includes a processor, for example, a processor operably coupled to a computer readable medium having stored thereon application software with computer executable instructions configured to transmit and receive communications form a from a network, application software with executable instructions for determining the blood volume using the method described herein, as well as application software with executable instructions optionally conducting a telemedicine session.

In some embodiments, networked device 320 includes a number of components, such as one or more processors and at least one communication module. In various embodiments, the one or more processors each include one or more processor cores. In various embodiments, the at least one communication module is physically and electrically coupled to the one or more processors. In further implementations, the communication module is part of the one or more processors. In various embodiments, networked device 320 include printed circuit board (PCB). For these embodiments, the one or more processors and communication module is disposed thereon.

Depending on its applications, networked device 320 includes other components that may or may not be physically and electrically coupled to the PCB. These other components include, but are not limited to, a memory controller, volatile memory (e.g., dynamic random access memory (DRAM)), non-volatile memory such as read only memory (ROM), flash memory, an I/O port, a digital signal processor, a crypto processor, a graphics processor, one or more antenna, a display, such as a touch screen display, a touch screen controller, a battery, an audio codec, a video codec, a global positioning system (GPS) device, a compass, an accelerometer, a gyroscope, a speaker, a camera, and a mass storage device (such as hard disk drive, a solid state drive, compact disk (CD), digital versatile disk (DVD), a microphone, and so forth. In some embodiments, the one or more processors is operatively coupled to system memory through one or more links (e.g., interconnects, buses, etc.). In embodiments, system memory is capable of storing information that the one or more processors utilizes to operate and execute programs and operating systems. In different embodiments, system memory is any usable type of readable and writeable memory such as a form of dynamic random access memory (DRAM). In embodiments, the networked device 320 includes a digital video camera configured to capture video and a microphone configured to capture audio. In embodiments, networked device 320 includes or is otherwise associated with various input and output/feedback devices to enable user interaction with the networked device 320 and/or peripheral components or devices associated with the networked device 320 by way of one or more user interfaces or peripheral component interfaces. In embodiments, the user interfaces include, but are not limited to a physical keyboard or keypad, a touchpad, a display device (touchscreen or non-touchscreen), speakers, microphones, image sensors, haptic feedback devices and/or one or more actuators, and the like. In embodiments, the display device is any type of output device that is able to present information in a visual form based on received electrical signals.

In some embodiments, the one or more processors, flash memory, and/or a storage device includes associated firmware storing programming instructions configured to enable the networked device 320, in response to execution of the programming instructions by one or more processors, to practice all or selected aspects of the methods described herein.

In embodiments, the communication module enables wired and/or wireless communications for the transfer of data to and from the networked device 320. In various embodiments, the networked device 320 also includes a network interface configured to connect the networked device 320 to one or more networked computing devices wirelessly via a transmitter and a receiver (or optionally a transceiver) and/or via a wired connection using a communications port. In embodiments, the network interface and the transmitter/receiver and/or communications port are collectively referred to as a "communication module". In embodiments, the wireless transmitter/receiver and/or transceiver may be configured to operate in accordance with one or more wireless communications standards. The term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some embodiments they might not. In embodiments, the networked device 320 includes a wireless communication module for transmitting to and receiving data, for example for transmitting and receiving data from a network, such as a telecommunications network. In examples, the communication module transmits data though a cellular network or mobile network, such as a Global System for Mobile Communications (GSM), General Packet Radio Service (GPRS), cdmaOne, CDMA2000, Evolution-Data Optimized (EV- DO), Enhanced Data Rates for GSM Evolution (EDGE), Universal Mobile Telecommunications System (UMTS), Digital Enhanced Cordless Telecommunications (DECT), Digital AMPS (IS-136/TDMA), and Integrated Digital Enhanced Network (iDEN), Long-Term Evolution (LTE), $3^{rd}$ generation mobile network (3G), 4th generation mobile network (4G), and/or 5th generation mobile network (5G) networks. In embodiments, the networked device 320 is directly connect with one or more devices via the direct wireless connection by using, for example, Bluetooth and/or BLE protocols, WiFi protocols, Infrared Data Association (IrDA) protocols, ANT and/or ANT+ protocols, LTE ProSe standards, and the like. In embodiments, the communications port is configured to operate in accordance with one or more known wired communications protocol, such as a serial communications protocol (e.g., the Universal Serial Bus (USB), FireWire, Serial Digital Interface (SDI), and/or other like serial communications protocols), a parallel communications protocol (e.g., IEEE 1284, Computer Automated Measurement And Control (CAMAC), and/or other like parallel communications protocols), and/or a network communications protocol (e.g., Ethernet, token ring, Fiber Distributed Data Interface (FDDI), and/or other like network communications protocols).

In embodiments, the networked device 320 and/or the monitoring module 160 is configured to run, execute, or otherwise operate one or more applications. In embodiments, the applications include native applications, web applications, and hybrid applications. For example, the native applications are used for operating the networked device 320 and/or the monitoring module 160, such as using a camera or other like sensor of the networked device 320 and/or the monitoring module 160, cellular phone functionality of the networked device 320 and/or the monitoring module 160, and other like functions of the networked device 320 and/or the monitoring module 160. In embodiments, native applications are platform or operating system (OS) specific or non-specific. In embodiments, native applications are developed for a specific platform using platform-specific development tools, programming languages, and the like. Such platform-specific development tools and/or programming languages are provided by a platform vendor. In embodiments, native applications are pre-installed on mobile computing devices 120 during manufacturing, or provided to the networked device 320 and/or the monitoring module 160 by an application server via a network. Web applications are applications that load into a web browser of the networked device 320 and/or the monitoring module 160 in response to requesting the web application from a service provider. In embodiments, the web applications are websites that are designed or customized to run on a mobile computing device by taking into account various mobile computing device parameters, such as resource availability, display size, touchscreen input, and the like. In this way, web applications may provide an experience that is similar to a native application within a web browser. Web applications may be any server-side application that is developed with any server-side development tools and/or programming languages, such as PHP, Node.js, ASP.NET, and/or any other like technology that renders HTML. Hybrid applications may be a hybrid between native applications and web applications. Hybrid applications may be a standalone, skeletons, or other like application containers that may load a website within the application container. Hybrid applications may be written using website development tools and/or programming languages, such as HTML5, CSS, JavaScript, and the like. In embodiments, hybrid applications use browser engine of the networked device 320 and/or the monitoring module 160, without using a web browser of the networked device 320 and/or the monitoring module 160, to render a website's services locally. In some embodiments, hybrid applications also access mobile computing device capabilities that are not accessible in web applications, such as the accelerometer, camera, local storage, and the like.

Any combination of one or more computer usable or computer readable medium(s) may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, etc.

Computer program code for carrying out operations of the present disclosure may be written in any combination of one or more programming languages, including an object-oriented programming language such as Java, Smalltalk, C++ or the like and conventional procedural programming languages, such as the "C" programming language or similar programming languages. The program code may execute entirely on the user's computing device, partly on the user's computing device, as a stand-alone software package, partly on the user's computing device and partly on a remote computing device or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Furthermore, example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium. A code segment may represent a procedure, a function, a subprogram, a program, a routine, a subroutine, a module, program code, a software package, a class, or any combination of instructions, data structures, program statements, and the like.

In various embodiments, an article of manufacture may be employed to implement one or more methods as disclosed herein. The article of manufacture may include a computer-readable non-transitory storage medium and a storage medium. The storage medium may include programming instructions configured to cause an apparatus to practice some or all aspects methods of determining blood volume, in accordance with embodiments of the present disclosure.

The storage medium may represent a broad range of persistent storage medium known in the art, including but not limited to flash memory, optical disks or magnetic disks. The programming instructions, in particular, may enable an apparatus, in response to their execution by the apparatus, to perform various operations described herein.

Figure 11:
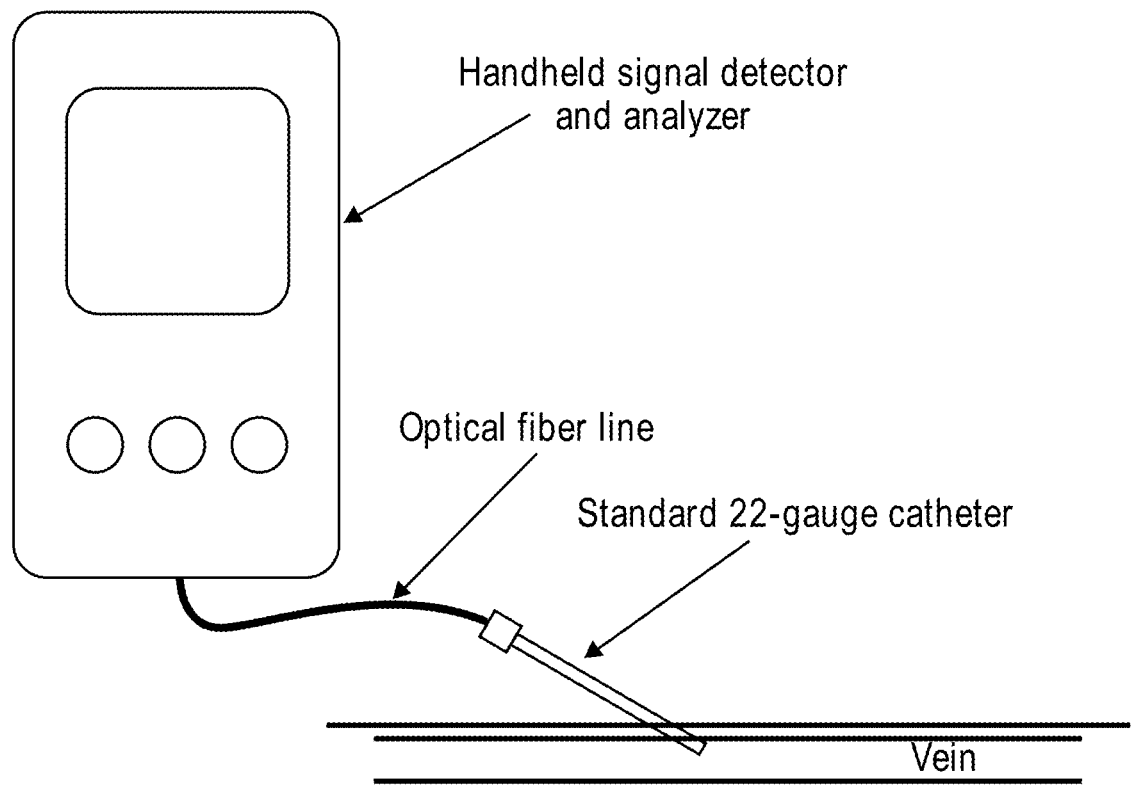
FIG. 11 is a schematic diagram of a handheld optical blood volume analyzer, in accordance with embodiments herein.

FIG. 11 is a schematic of a hand-held device. The optical fiber line and catheter would be disposable components. The injected ICG would come in lyophilized form in a pre-loaded 5 ml syringe. The syringe would be attached to an IV catheter (separate from above), patient blood would be withdrawn into the ICG-containing syringe, then injected back into the patient.

Figure 12:
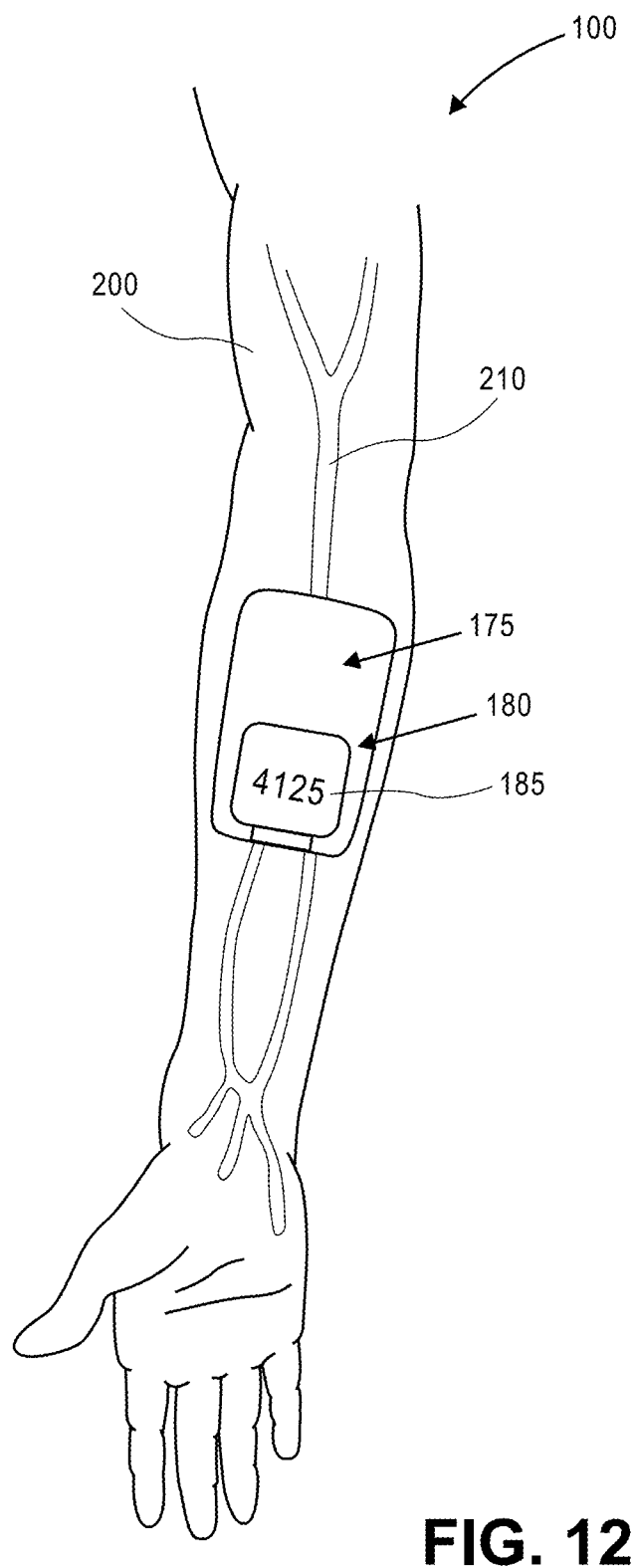
FIG. 12 is a schematic diagram of a compact analyzer that attaches to a light impermeable adhesive pad.

FIG. 12 is a schematic of a mobile blood volume analyzer 100, in accordance with embodiments disclosed herein. In this embodiment, the mobile blood volume analyzer 100 attaches to the arm 200 of a subject, with a disposable adhesive patch 175 that blocks ambient light and has a docking site 180 for the device. Adhesives and methods of their use are known in the art. In the embodiment shown, the components of the worn part of the mobile blood volume analyzer 100, including a mini-spectrophotometer, a light source, such as a LED light source are part of the display device 185. The mobile blood volume analyzer 100 further includes a fiber optic cable that couples the mini spectrophotometer to an intravenous probe, as described above. The intravenous probe is configured to capture the reflected light from an indicator that has been injected into the subject. In embodiments, intravenous probe is configured to be disposable, for example configured for a single use, such as for a single subject. In certain embodiments, the fiber optic cable is configured to be disposable and is reversibly coupled to the mini spectrophotometer, which is not configured to be a disposable component of the device. In this embodiment, the mobile blood volume analyzer is configured to display results on a small read-out screen, for example roughly the size of a watch face, in order to simplify and avoid the need for transmission to a smartphone or other device. The results displayed may include total blood volume, plasma volume, red cell volume, Hb, Hct, $SvO_2$ and other clinically relevant parameters. In embodiments, the disposable optical fiber component is inserted into a vessel through an intravascular catheter and secured via luer lock. The disposable, light impermeable adhesive pad is secured onto the skin proximal to the catheter insertion site, covering the optical fiber terminus. The optical fiber origin is then connected to the reusable compact device and the compact device is attached to the adhesive pad via a docking site on the outer surface of the pad adjacent to the catheter insertion site. The remainder of the device works as described above.

Also provided is a system for determining blood volume of a subject. In an embodiment, the system includes a blood volume analyzer such as described herein. In embodiments, the system may include a mobile electronic device communicatively coupled to the blood volume analyzer. In embodiments, the system includes one or more processor, for example, as part of the blood volume analyzer, and a computer-readable storage device storing instructions executable by the computer processor for the methods described herein. It is understood that separate embodiments of the system for determining blood volume of a subject comprise herein each of the independent embodiments in which the system's blood volume analyzer, mobile electronic device communicatively coupled to the blood volume analyzer, processor, and computer-readable storage device for storing instructions executable by the computer processor are as described in each instance herein.

For example, in some embodiments, the blood volume analyzer of the system is a mobile blood volume analyzer. In some embodiments, the blood volume analyzer comprises a mini-spectrometer. In some embodiments, the blood volume analyzer comprises a light source, such as a LED light source. In some embodiments the mobile blood volume analyzer may be configured to display results on a read-out screen, for example, instead of, or in conjunction with, the mobile computing device.

In some embodiments, the system for determining blood volume of a subject includes an optical fiber probe to measure the reflectance of an injected blood volume indicator that may be positioned intravenously. In some embodiments, the optical fiber probe is a catheterized optical fiber probe. In some embodiments, the optical fiber probe includes a fiber optic cable that is or may be coupled to a mini-spectrometer. In some embodiments, the optical fiber probe comprises a fiber optic cable that is or may be reversibly coupled to a mini-spectrometer.

In some embodiments of the system, the blood volume analyzer includes an armband for securing the blood volume analyzer to the arm of a subject. In some embodiments the armband in the devices and systems herein is a durable armband, i.e. the armband comprises materials and means that allow it to be attached to the arms of a subject and removed multiple times for repeated uses. In some embodiments, the armband may be capable of passing around a subject's arm and secured in position through hook and loop means, such as a VELCRO® Brand hook and loop product. In other embodiments, the armband may be secured on a subject's arm through an adjustable strap and buckle means. In some embodiments the armband may be secured by a quick-release strap and buckle means.

Also provided is a kit for use with the devices and systems herein, particularly for a single use with the devices and systems herein. In some embodiments the kit includes one or more containers holding a volume of blood volume indicator sufficient for use in determining the blood volume of a subject using a device or system described herein. In embodiments, the kit includes an intravenous probe useful for a device or system as disclosed herein, and instructions for use of the blood volume indicator and the intravenous probe with a device or system described herein. In some embodiments, the kit includes a volume of indocyanine green (ICG) sufficient for use as the blood volume indicator in conjunction with a device or system herein. In some embodiments, the kit includes a syringe for administration of the blood volume indicator, such as ICG, intravenously to a subject for whom a blood volume status is desired and/or needed. In some embodiments, the kit includes an intravenous catheter (which may also be referred to as a peripheral venous catheter, peripheral venous line or a peripheral venous access catheter), the intravenous catheter being capable of mating with a syringe or tubing means to introduce a volume of blood volume indicator intravenously to a subject. In additional embodiments, the kit includes an intravenous probe for insertion into a blood vessel of a subject. In additional embodiments, the kit includes an optical fiber for connecting the intravenous probe to a detector (photospectrometer or photodetectors) used in a device or system described herein. In some embodiments, the kit comprises: a container holding a volume of blood volume indicator; a syringe for administration of the blood volume indicator; an intravenous catheter; an intravenous probe; an optical fiber for connecting the intravenous probe to a detector; and directions for using each of the elements of the kit in conjunction with a device or system described herein to determine the blood volume of a subject.

The following example is provided to illustrate certain particular features and/or embodiments. This example should not be construed to limit the invention to the particular features or embodiments described.

EXAMPLE

Figure 6:
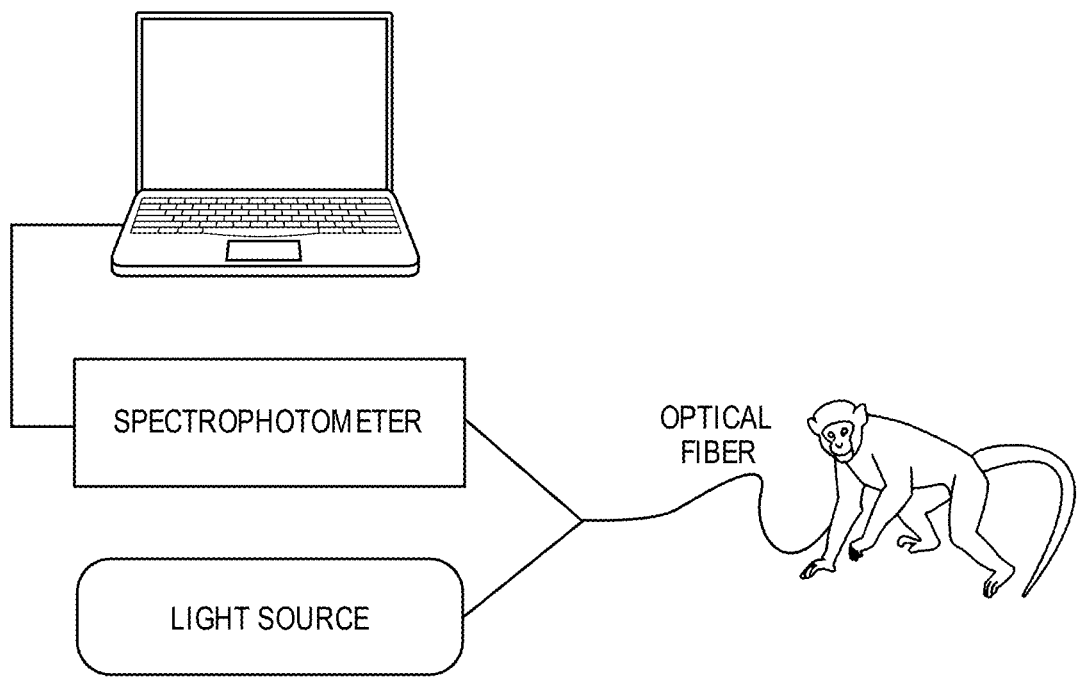
FIG. 6 shows a schematic of an optical blood volume analyzer that used a spectrophotometer and full-spectrum light source connected in a dual optical fiber configuration, in accordance with embodiments herein. The end of the fiber probe was positioned in the cephalic vein by threading the fibers through a standard 22 gauge, 1" intravenous catheter. The probe was secured in place with a standard luer lock connector.
Figure 7:
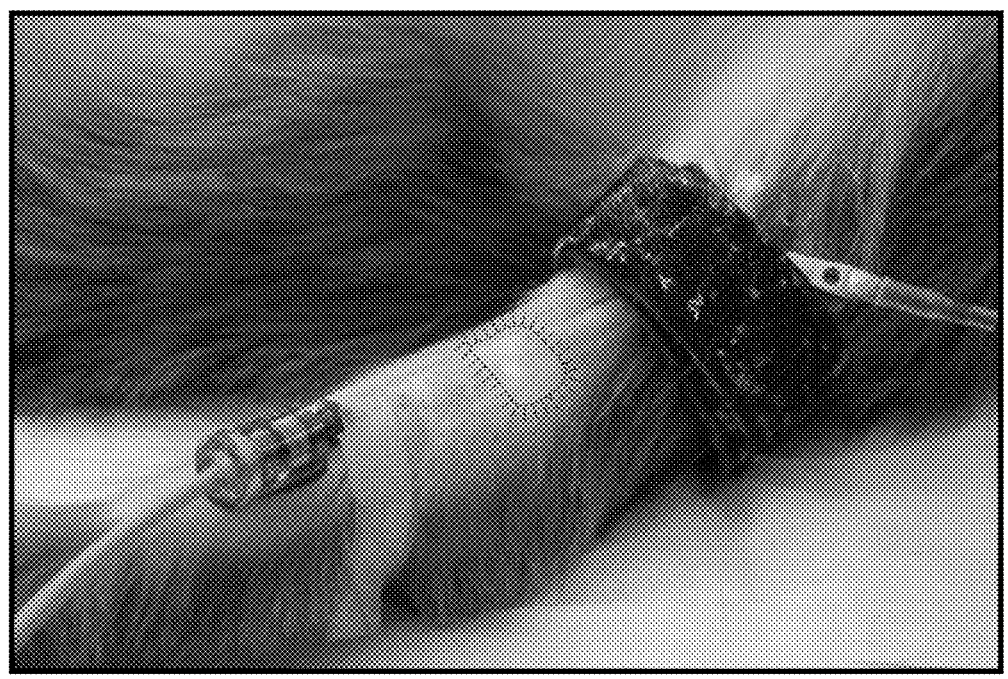
FIG. 7 is a digital image showing an optical blood volume analyzer probe inserted through a 22-gauge catheter in the cephalic vein of a rhesus macaque. The optical fiber probe is connected to a light source and a spectrophotometer. Blood volume indicator dilution and elimination rates were determined over approximately 7 minutes using the optical blood volume analyzer.

A prototype analyzer was used to intravenously position an optical fiber probe to measure the reflectance of an injected fluorophore or chromophore blood volume indicator (see FIGS. 6 and 7). The dilution of the blood volume indicator is directly proportional to the diluent (blood) volume as expressed by conservation of matter.

Figure 8:
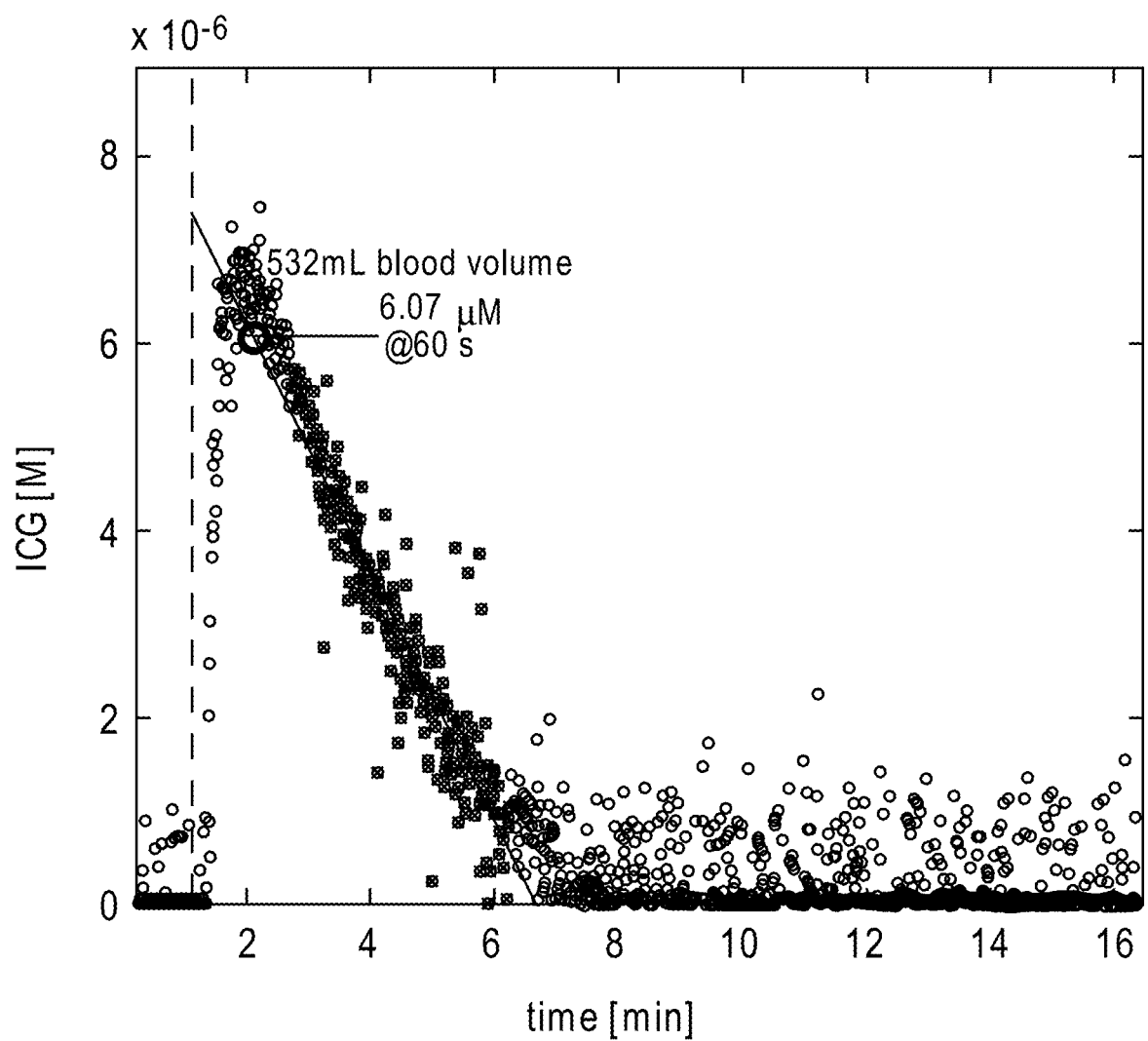
FIG. 8 is a graph of raw data showing ICG concentration after intravenous injection (indicated by vertical dashed line at t≈1 min). The initial mixing of ICG in blood can be seen as the peak and the rapid elimination of ICG by the liver represented by the negative slope of the darkened data points. Only the darkened data points were used for the regression to the timepoint at which the measured concentration of ICG equals the theoretical concentration of ICG if perfect mixing and no elimination occurred at the time of injection (see black circle at t≈2 min indicating 532 mL blood volume). This timepoint is typically 1 minute after the time of ICG injection, putatively due to the delay before sufficient mixing of the ICG in the blood which enables the onset of ICG removal by the liver.

The subjects were 5 healthy adult rhesus macaques. An exemplary graph of raw data is shown in FIG. 8. Indicator elimination rate was determined and mathematical regression was used to calculate the theoretical concentration of the indicator had it been perfectly mixed and distributed in circulating blood at the time of injection. Concentration dilution mathematics was then used to determine the total blood volume of each subject. Repeat measurements were assessed to roughly evaluate reproducibility. Results were also compared to validated formulas used to estimate blood volume in this species.

Figure 9:
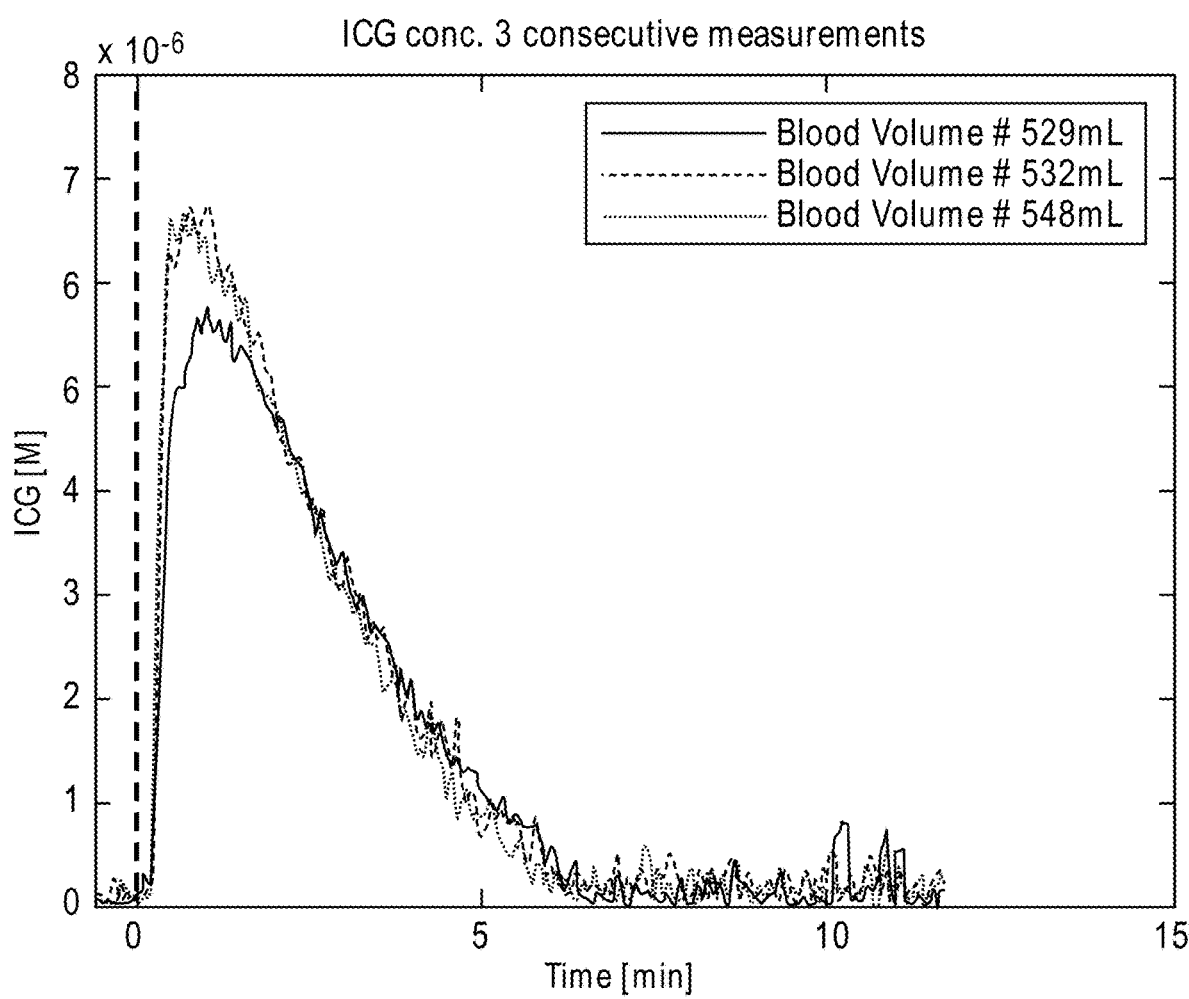
FIG. 9 shows an example data set of 3 consecutive blood volume measurements in an animal subject. Reflectance of the injected blood volume indicator (ICG in this case) was measured every 2 seconds. Variation in peak values within the first minute after injection is an artifact due to variations in the mixing of the blood volume indicator in circulation after injection. Regression of the rate of blood volume indicator elimination to the time of injection was used to calculate the theoretical concentration of the blood volume indicator in blood at the time of injection, before any elimination. This concentration was then used to determine blood volume. The mean and standard deviation of the 3 trials were 535.7+/−9.1 mL. For reference, the expected blood volume was 533 ml.
Figure 10:
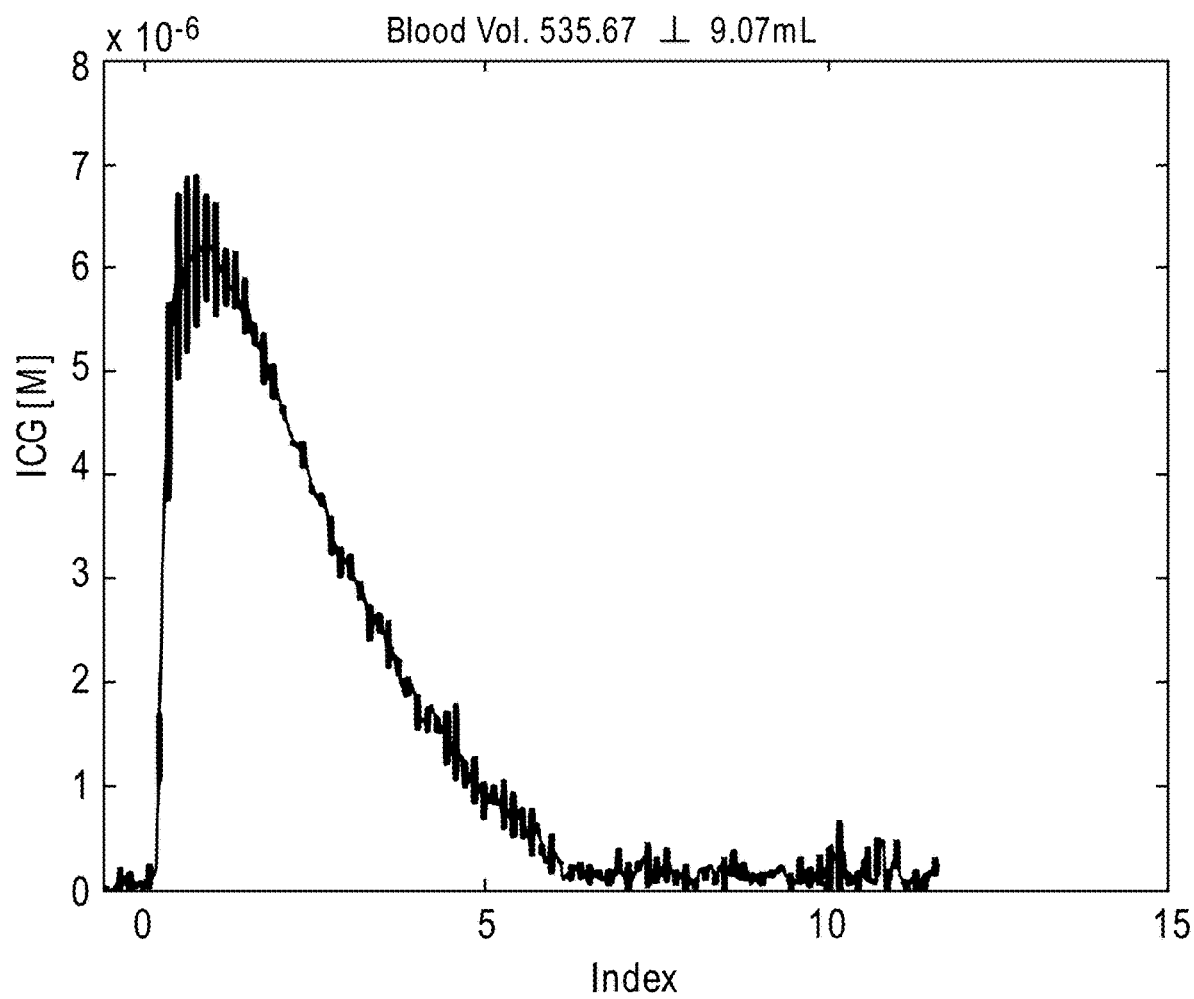
FIG. 10 shows the same data as FIG. 9, but as the mean and standard deviation of the three measurements.

None of the subjects experienced any deleterious effects from the testing protocol during the procedures or during a 3-day follow-up period of observation. Up to 6 repeat measures were completed with each subject during testing periods of less than 3 hours. A total of 44 tests were completed. Blood volume indicator values returned to baseline (non-detectable) after approximately 10 minutes and repeat measures were successfully taken every 15 minutes. Repeat measures were generally consistent. Blood volume results were within 8% of the expected blood volume based upon validated formulas used to estimate blood volume in this species. (Hobbs, et al., J Amer Assoc Lab Animal Sci, Vol 54, No. 6, November 2015, pp. 687-693). An example data set is shown in FIGS. 8 and 9.

This in vivo dilution detection method is a novel approach that will provide patient blood volume and other diagnostically relevant information, such as Hb, PV, RV, Hct, and/or $SvO_2$, within a few minutes with no blood sampling or laboratory processing. The rapid acquisition of patient blood volume will allow clinicians to utilize this information for immediate decision making as well as enable progressive monitoring of blood volume to assess the effectiveness of therapeutic interventions. Embodiments will yield a small, rugged device amenable to a smartphone interface.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A method comprising:
receiving data that includes an optical magnitude of a blood volume indicator in blood of a subject over time;
determining a time course for a concentration of the blood volume indicator using the optical magnitude of the blood volume indicator over time and a known volume and concentration of the blood volume indicator prior to injection into the blood of the subject;
fitting the time course for the concentration of the blood volume indicator to a model of the concentration of the blood volume indicator decreasing as a function of time;
determining a total initial concentration of the blood volume indicator in the blood if the blood volume indicator were mixed instantaneously with the blood;
determining a total blood volume, wherein the total blood volume is based on the known concentration of the blood volume indicator prior to injection, the known volume of the blood volume indicator, and the total initial concentration of the blood volume indicator in the blood if the blood volume indicator were mixed instantaneously with the blood;
acquiring a pre-injection reflectance spectrum for use as a baseline control, wherein detecting the optical magnitude of the blood volume indicator comprises detecting an optical reflectance of the blood volume indicator; and
determining a pre-injection computed reference spectrum that simulates the pre-injection reflectance spectrum; wherein determining the time course additionally uses the pre-injection computed reference spectrum.

2. The method of claim 1, wherein determining the pre-injection computed reference spectrum that simulates the pre-injection reflectance spectrum comprises modeling the pre-injection reference spectrum with $R_{before.BVI}$=getR $(\mu_a, \mu_s')$, wherein $$\mu_s'(\lambda) = \mu_s'(500 \text{ nm})\left(\frac{500 \text{ nm}}{\lambda}\right)$$

as normalized at 500 nm and $\mu_a(\lambda)=s\mu_{a.oxy}(\lambda)+(1-S)\mu_{a.deoxy}(\lambda)+W\mu_{a.water}(\lambda)$, wherein $\mu_s'(\lambda)$ is an optical scattering coefficient of blood per wavelength, S is hemoglobin oxygen saturation, W is water content, $\mu_{a.oxy}(\lambda)$ is an absorption spectrum of fully oxygenated whole blood, $\mu_{a.deoxy}(\lambda)$ is an absorption spectrum of fully deoxygenated whole blood, and $\mu_{a.water}(\lambda)$ is an absorption spectrum of water.

3. The method of claim 2, further comprising determining one or more of: a pre-injection oxygen saturation (S), hemoglobin concentration (Hb), venous oxygen saturation ($SvO_2$), lactate, hematocrit (Hct), plasma volume (PV), and red cell volume (RV).

4. The method of claim 1, further comprising receiving the optical magnitude of the blood volume indicator over time and acquiring a set of two or more post-injection reflectance spectra over a time period T1.

5. The method of claim 4, further comprising determining a post-injection computed reflectance spectrum for each of the two or more post-injection reflectance spectra.

6. The method of claim 5, wherein determining the post-injection computed reflectance spectrum that simulates a post-injection reflectance spectrum comprises modeling the post-injection reflectance spectrum with $R_{after.BVI}(t) = \text{getR}(\mu_a + \mu_{a.BVI}(t), \mu_s')$, where $\mu_{a.BVI}(t) = C_{BVI}(t) \, \varepsilon_{BVI} \ln(10)[\text{cm}^{-1}]$, thereby determining a $C_{BVI}$ for each of the two or more post-injection reflectance spectra.

7. The method of claim 4, wherein acquiring the set of two or more post-injection reflectance spectra over the time period T1 comprises measuring a reflectance of the blood volume indicator every two seconds for the time period T1.

8. The method of claim 7, wherein the time period T1 is between one and fifteen minutes.

9. The method of claim 1, wherein the blood volume indicator is a fluorophore or chromophore that is contained within microbubbles.

10. The method of claim 1, wherein the blood volume indicator comprises indocyanine green.

11. The method of claim 1, further comprising an optical blood volume analyzer configured to detect the optical magnitude of the blood volume indicator.

12. The method of claim 11, wherein the optical blood volume analyzer includes a transdermal detector configured to detect the data that includes the optical magnitude of the blood volume indicator from through skin of the subject.

13. The method of claim 11, wherein the optical blood volume analyzer comprises a detector for detecting the spectrum of the blood volume indicator.

14. The method of claim 13, wherein the detector comprises a spectrophotometer.

15. The method of claim 11, wherein the optical blood volume analyzer comprises an intravenous probe for insertion into a blood vessel of the subject.

16. The method of claim 15, wherein the optical blood volume analyzer further comprises an optical fiber connected to the detector and disposed within the intravenous probe.

17. The method of claim 11, further comprising placing an adhesive patch onto skin of the subject over an optical fiber terminus where the optical magnitude of the blood volume indicator is optically detected, wherein the adhesive patch blocks ambient light and has a docking site for the optical blood volume analyzer.

18. The method of claim 15, wherein the intravenous probe comprises a peripheral venous access catheter capable of mating with a syringe or tubing.

19. The method of claim 15, wherein the optical blood volume analyzer comprises at least first and second optical fibers configured to be placed via intravascular catheter such that the first optical fiber is configured to deliver light and the second optical fiber is configured to collect light.

20. The method of claim 19, wherein the first optical fiber is among one or more optical fibers configured to deliver light, and the second optical fiber is among a plurality of optical fibers configured to collect light and disposed surrounding the one or more optical fibers configured to deliver light.

21. The method of claim 19, wherein the second optical fiber is among one or more optical fibers configured to collect light, and the first optical fiber is among a plurality of optical fibers configured to deliver light and disposed surrounding the one or more optical fibers configured to collect light.

22. The method of claim 11, wherein the optical blood volume analyzer further comprises a light source for illuminating the blood volume indicator.

23. The method of claim 11, wherein the optical blood volume analyzer further comprises an armband.

24. The method of claim 11, wherein the optical blood volume analyzer further comprises a monitoring component.

25. The method of claim 11, wherein the optical blood volume analyzer further comprises an injector for injecting the blood volume indicator.

26. The method of claim 1, wherein the blood volume indicator is a first blood volume indicator, the method further comprising injecting one or more additional blood volume indicators to determine one or more additional components of blood volume, the one or more additional components of the blood volume including one or more of: circulating volume, a difference between total volume and circulating volume, marginal pool, and glycocalyx.

27. The method of claim 1, further comprising repeating the method to one or both of receive the data that includes the optical magnitude of the blood volume indicator in the blood of the subject over time and determine the total blood volume based on the repeated receipt of the data that includes the optical magnitude of the blood volume indicator in the blood of the subject over time.

28. The method of claim 1, wherein fitting the time course for the concentration of the blood volume indicator to the model of the concentration of the blood volume indicator decreasing as a function of time, thereby determining the total initial concentration of the blood volume indicator in the blood, comprises using regression to fit the time course for the concentration of blood volume indicator to the equation:

$$C_{BVI}(t) = C_{BVI1.0}(1 - e^{-t/t_{mix}})e^{-t/t_{clearance}}$$

wherein $C_{BVI}(t)$ is a concentration of the blood volume indicator at time t, $C_{BVI1.0}$ is a total initial concentration of the blood volume indicator in the blood if the blood volume indicator were mixed instantaneously with the blood, $t_{mix}$ is a mixing time constant of the blood volume indicator in the blood, and $t_{clearance}$ is a time constant for elimination of the blood volume indicator from the blood.

29. A device comprising:
a photospectrometer for detecting an optical magnitude of a blood volume indicator in blood of a subject over time;
an intravenous probe for insertion into a blood vessel of a subject;
a first optical fiber disposed within the intravenous probe and connected to a light source positioned to illuminate the blood volume indicator;
a second optical fiber disposed within the intravenous probe and connected to the photospectrometer, and an output configured to output the optical magnitude of the blood volume indicator; and
a processor configured for
determining a time course for a concentration of the blood volume indicator using the magnitude of the optical reflectance over time, and a known volume and concentration of the blood volume indicator prior to injection into the blood of the subject;
fitting the time course for the concentration of the blood volume indicator to a model of the concentration of the blood volume indicator decreasing as a function of time, thereby determining a total initial concentration of the blood volume indicator in the blood if the blood volume indicator were mixed instantaneously with the blood;
determining a total blood volume, wherein the total blood volume ($V_{tot}$) is equal to the known concentration of the blood volume indicator prior to injection, multiplied by the known volume of the blood volume indicator, divided by the total initial concentration of the blood volume indicator in the blood if the blood volume indicator were mixed instantaneously with the blood;

acquiring a pre-injection reflectance spectrum for use as a baseline control, wherein detecting the optical magnitude of the blood volume indicator comprises detecting an optical reflectance of the blood volume indicator; and determining a pre-injection computed reference spectrum that simulates the pre-injection reflectance spectrum;

wherein determining the time course additionally uses the pre-injection computed reference spectrum.

30. The device of claim 29, further comprising an armband or an adhesive mount.

31. The device of claim 29, further comprising a monitoring component.

32. The device of claim 29, further comprising an injector for injecting the blood volume indicator.

33. The device of claim 29, wherein the light source emits light in the near infrared spectrum, and wherein the photospectrometer detects the optical magnitude of the blood volume indicator in the near infrared spectrum.

34. A system comprising:

a detector for detecting an optical magnitude of a blood volume indicator in blood of a subject over time; and a processor configured for:

determining a time course for a concentration of the blood volume indicator using the optical magnitude over time, and a known volume and concentration of the blood volume indicator prior to injection into the blood of the subject;

fitting the time course for the concentration of the blood volume indicator to a model of the concentration of the blood volume indicator decreasing as a function of time, thereby determining a total initial concentration of the blood volume indicator in the blood if the blood volume indicator were mixed instantaneously with the blood;

determining a total blood volume, wherein the total blood volume ($V_{tot}$) is equal to the known concentration of the blood volume indicator prior to injection, multiplied by the known volume of the blood volume indicator, divided by the total initial concentration of the blood volume indicator in the blood if the blood volume indicator were mixed instantaneously with the blood;

acquiring a pre-injection reflectance spectrum for use as a baseline control, wherein detecting the optical magnitude of the blood volume indicator comprises detecting an optical reflectance of the blood volume indicator; and determining a pre-injection computed reference spectrum that simulates the pre-injection reflectance spectrum;

wherein determining the time course additionally uses the pre-injection computed reference spectrum.

35. The system of claim 34, further comprising a communication component connected to the detector and configured to transmit data to a networked device configured for communicating via a network.

36. The system of claim 34, wherein the detector comprises:

a photospectrometer;

a light source;

an intravenous probe for insertion into a blood vessel of a subject;

a first optical fiber disposed within the intravenous probe and connected to the light source; and a second optical fiber disposed within the intravenous probe and connected to the photospectrometer.

37. The system of claim 36, wherein the light source emits light in the near infrared spectrum, and wherein the photospectrometer detects the optical magnitude of the blood volume indicator in the near infrared spectrum.

* * * * *

UNITED STATES PATENT AND TRADEMARK OFFICE
CERTIFICATE OF CORRECTION

| | |
|---|---|
| PATENT NO. | : 11,284,823 B2 |
| APPLICATION NO. | : 16/233488 |
| DATED | : March 29, 2022 |
| INVENTOR(S) | : Theodore Hobbs, Ravikant Samatham and Steven L. Jacques |

It is certified that error appears in the above-identified patent and that said Letters Patent is hereby corrected as shown below:

In the Specification

At Column 1, Lines 12-17, delete the following paragraph:
"STATEMENT OF GOVERNMENT INTEREST
This invention was made with government support under UL1TR000128 and P51OD01192 awarded by the National Institutes of Health (NIH). The government has certain rights in the invention."

And replace it with the following:
--ACKNOWLEDGEMENT OF GOVERNMENT SUPPORT
This invention was made with government support under TR000128 and P51 OD011092 awarded by The National Institutes of Health. The government has certain rights in the invention.--

Signed and Sealed this
Fourteenth Day of October, 2025

John A. Squires
*Director of the United States Patent and Trademark Office*